(12) United States Patent
Yamamoto

(10) Patent No.: US 10,383,601 B2
(45) Date of Patent: Aug. 20, 2019

(54) ACOUSTIC WAVE PROCESSING APPARATUS, SIGNAL PROCESSING METHOD, AND PROGRAM FOR ACOUSTIC WAVE PROCESSING APPARATUS

(71) Applicant: FUJIFILM Corporation, Tokyo (JP)

(72) Inventor: Hiroaki Yamamoto, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 425 days.

(21) Appl. No.: 15/254,158

(22) Filed: Sep. 1, 2016

(65) Prior Publication Data

US 2016/0367222 A1 Dec. 22, 2016

Related U.S. Application Data

(63) Continuation of application No. PCT/JP2014/081731, filed on Dec. 1, 2014.

(30) Foreign Application Priority Data

Mar. 31, 2014 (JP) .................. 2014-071550

(51) Int. Cl.
*A61B 8/00* (2006.01)
*A61B 8/08* (2006.01)
(Continued)

(52) U.S. Cl.
CPC ............ *A61B 8/5207* (2013.01); *A61B 8/145* (2013.01); *A61B 8/4488* (2013.01); *A61B 8/461* (2013.01);
(Continued)

(58) Field of Classification Search
CPC ....... A61B 8/14; A61B 8/5207; A61B 8/4488; A61B 8/4483; A61B 8/461; A61B 8/54;
(Continued)

(56) References Cited

U.S. PATENT DOCUMENTS

2006/0241456 A1* 10/2006 Karasawa ................ A61B 8/14
600/447
2009/0182235 A1 7/2009 Robert et al.
(Continued)

FOREIGN PATENT DOCUMENTS

| JP | 58-44372 A | 3/1983 |
| JP | 2009-536853 A | 10/2009 |
| JP | 2014-30715 A | 2/2014 |

OTHER PUBLICATIONS

English Translation of International Preliminary Report on Patentability (including PCT/IB/373 and PC/ISA/237) for PCT/JP2014/081731, dated Oct. 4, 2016.
(Continued)

*Primary Examiner* — Bill Thomson
*Assistant Examiner* — Aminah Asghar
(74) *Attorney, Agent, or Firm* — Birch, Stewart, Kolasch & Birch, LLP

(57) ABSTRACT

There are included a data-processing-unit that selects two or more pieces of data from among a plurality of pieces of first element data or from among a plurality of pieces of first reception data generated by subjecting the pieces of first element data to phasing addition processing and that performs superimposition processing on the two or more pieces of data to generate processed data, an image-generation-unit that generates an acoustic wave image on the basis of the processed data, a setting-information-holding-unit that holds setting information on at least one of a transmitting-unit, a receiving-unit, the data-processing-unit, the-image-generation-unit, and a display-control-unit, and a setting-changing-unit that, in a case where a measurement condition is changed, changes setting of at least one of the transmitting-unit, the receiving-unit, the data-processing-unit, the image-generation-unit, and the display-control-unit on the basis of
(Continued)

the held setting information, the setting being related to the acoustic wave image generated on the basis of the processed data.

18 Claims, 12 Drawing Sheets

(51) Int. Cl.
  *G01S 7/52* (2006.01)
  *G01S 15/89* (2006.01)
  *A61B 8/14* (2006.01)
(52) U.S. Cl.
  CPC ............ *A61B 8/54* (2013.01); *G01S 7/52047* (2013.01); *G01S 7/52095* (2013.01); *G01S 15/8915* (2013.01); *A61B 8/14* (2013.01)
(58) Field of Classification Search
  CPC ............... G10K 11/346; G01S 15/8915; G01S 7/52046; G01S 7/52095; G01S 7/52047
  See application file for complete search history.

(56) References Cited

U.S. PATENT DOCUMENTS

| | | | | |
|---|---|---|---|---|
| 2014/0140600 | A1* | 5/2014 | Daigle | ................... G06T 5/001 382/131 |
| 2015/0141831 | A1 | 5/2015 | Yamamoto | |
| 2015/0351720 | A1* | 12/2015 | Ikeda | ................... A61B 8/5269 600/447 |

OTHER PUBLICATIONS

International Search Report, issued in PCT/JP2014/081731, dated Mar. 3, 2015.
Written Opinion of the International Searching Authority, issued in PCT/JP2014/081731 (PCT/ISA/237), dated Mar. 3, 2015.
Japanese Office Action, dated Oct. 4, 2016, for Japanese Application No. 2014-071550 is provided, as well as an English translation.

* cited by examiner

FIG. 4B
ELEMENT DATA
FIG. 4D
ELEMENT DATA
NO SIGNAL
FIG. 4A
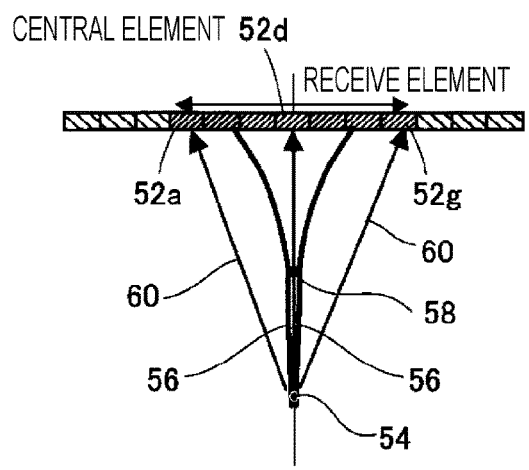
FIG. 4C
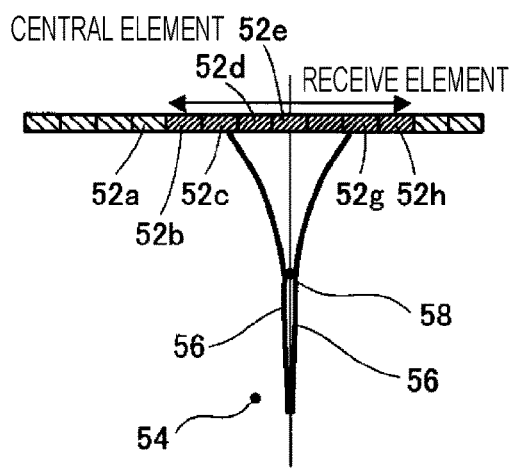
FIG. 5B
ELEMENT DATA
FIG. 5D
ELEMENT DATA
GHOSTING
FIG. 5A
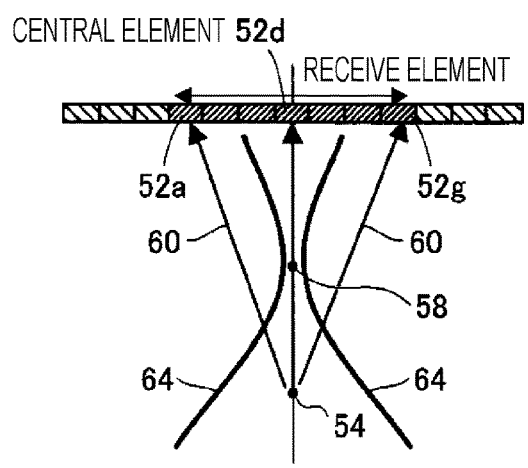
FIG. 5C
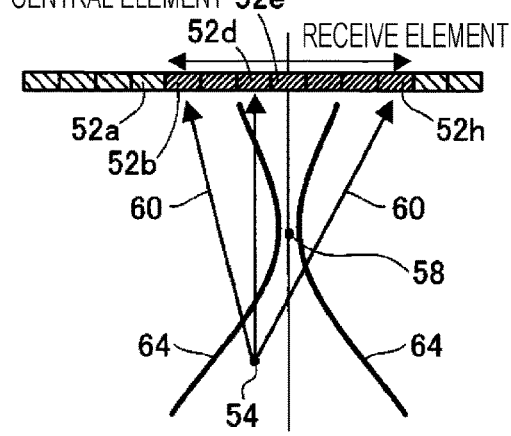

ACOUSTIC WAVE PROCESSING APPARATUS, SIGNAL PROCESSING METHOD, AND PROGRAM FOR ACOUSTIC WAVE PROCESSING APPARATUS

CROSS-REFERENCE TO RELATED APPLICATIONS

This application is a Continuation of PCT International Application No. PCT/JP2014/081731 filed on Dec. 1, 2014, which claims priority under 35 U.S.C § 119 (a) to Japanese Patent Application No. 2014-071550 filed on Mar. 31, 2014. Each of the above application(s) is hereby expressly incorporated by reference, in its entirety, into the present application.

BACKGROUND OF THE INVENTION

1. Field of the Invention

The present invention relates to an acoustic wave processing apparatus, a signal processing method, and a non-transitory computer readable recording medium storing a program for imaging an inspection object, such as an organ in a living body, by transmitting and receiving acoustic wave beams to generate acoustic wave images or the like used for the examination or diagnosis of the inspection object.

2. Description of the Related Art

In the field of medicine, acoustic-wave diagnostic apparatuses, such as ultrasonic image diagnostic apparatuses, that generate ultrasound images used for the examination or diagnosis of an inspection object by using acoustic waves, such as ultrasonic waves, are conventionally put to practical use.

This type of ultrasonic diagnostic apparatus typically has an ultrasonic probe (ultrasonic probe unit: hereinafter also referred to as "probe") having a plurality of elements (ultrasonic transducers) built therein, and an apparatus body connected to the probe. The ultrasonic diagnostic apparatus transmits ultrasonic beams from the plurality of elements of the probe toward a subject (an inspection object) so as to form a predetermined focal point (transmit focal point), receives ultrasonic echoes from the subject by using the probe, and electrically processes reception signals of the received ultrasonic echoes by using the apparatus body to thereby generate an ultrasound image.

An ultrasonic beam is transmitted on the basis of a predetermined transmit delay pattern so as to drive a plurality of elements to form a set focal point. Such an ultrasonic beam is shaped to be wide in the lateral direction. This causes a problem in that information on a reflection point located at a laterally shifted position may be picked up and reproduced on an ultrasound image as a so-called "ghost" signal.

To address this problem, in the ultrasonic diagnostic apparatus, the generation of a single ultrasound image includes superimposing a plurality of pieces of data (element data or reception data) obtained via individual transmissions in accordance with reception times or the positions of the elements and correcting the pieces of data, called multi-line processing (JPS58-44372A (JP1983-44372A) and JP2009-536853A). Ghost signals are removable because the ghost signals are superimposed while being shifted with respect to each other and cancel each other out even if pieces of data are superimposed in accordance with reception times or the positions of the elements.

SUMMARY OF THE INVENTION

If a probe is changed in an ultrasonic diagnostic apparatus that performs multi-line processing, the number of pieces of data to be superimposed in multi-line processing or image brightness information and so on that vary depending on the number of pieces of data to be superimposed are not succeeded. This causes a problem such as varying lightness of an ultrasound image to be displayed or a largely varying frame rate before and after the change of the probe.

In addition, if transmit conditions such as the position of the transmit focal point are changed, the number of pieces of data to be superimposed in multi-line processing or image brightness information and so on that vary depending on the number of pieces of data to be superimposed on the basis of information such as the changed position of the transmit focal point are also not succeeded. This also causes a problem such as varying lightness of an ultrasound image to be displayed or a largely varying frame rate before and after the change of the transmit conditions.

This requires repeated setting to be performed each time a probe or a transmit condition is changed, causing a problem such as increased complexity of operation or a long examination time.

It is an object of the present invention to overcome the problems with the conventional technique described above and to provide an acoustic wave processing apparatus, a signal processing method, and a non-transitory computer readable recording medium storing a program that can prevent, if a probe or a transmit condition is changed in an ultrasonic diagnostic apparatus which performs multi-line processing, a large change in image lightness or frame rate before and after the change.

As a result of intensive studies to achieve the foregoing object, the inventor has found that the problems described above can be overcome by the provision of a data processing unit that selects two or more pieces of data from among a plurality of pieces of first element data, or a plurality of pieces of first reception data generated by subjecting the pieces of first element data to phasing addition processing and that performs superimposition processing on the two or more pieces of data to generate processed data, an image generation unit that generates an acoustic wave image on the basis of the processed data generated by the data processing unit, a display control unit that causes a display unit to display the generated acoustic wave image, a setting information holding unit that holds setting information on at least one of the transmitting unit, the receiving unit, the data processing unit, the image generation unit, and the display control unit, and a setting changing unit that, in a case where a measurement condition is changed, changes setting of at least one of the transmitting unit, the receiving unit, the data processing unit, the image generation unit, and the display control unit on the basis of the setting information held in the setting information holding unit.

Specifically, the present invention provides (1) to (13) as follows.

(1) An acoustic wave processing apparatus including:
a probe unit having a plurality of elements arranged therein, the probe unit being configured to transmit an acoustic wave beam, receive an acoustic wave echo reflected by an inspection object, and output an analog element signal corresponding to the received acoustic wave echo;
a transmitting unit that causes the probe unit to perform a plurality of times an operation of transmitting the acoustic wave beam by using two or more elements among the plurality of elements as transmit elements so as to form a predetermined transmit focal point;
a receiving unit that receives an acoustic echo corresponding to each transmission of the acoustic beam with two or more elements among the plurality of elements as reception elements, receives analog element signals output from the reception elements, and performs predetermined processing on the analog element signals;

an A/D conversion unit that performs A/D conversion on the analog element signals processed by the receiving unit to convert the analog element signals to first element data as a digital element signal;

a data processing unit that selects two or more pieces of data from among a plurality of pieces of the first element data output by the A/D conversion unit or from among a plurality of pieces of first reception data generated by performing phasing addition processing on the first element data and performs superimposition processing on the selected two or more pieces of data to generate processed data;

an image generation unit that generates an acoustic wave image on the basis of the processed data generated by the data processing unit;

a display control unit that causes a display unit to display the generated acoustic wave image;

a setting information holding unit that holds setting information on at least one of the transmitting unit, the receiving unit, the data processing unit, the image generation unit, and the display control unit; and a setting changing unit that, in a case where a measurement condition is changed, changes setting of at least one of the transmitting unit, the receiving unit, the data processing unit, the image generation unit, and the display control unit on the basis of the setting information held in the setting information holding unit, the setting being related to the acoustic wave image generated on the basis of the processed data.

(2) The acoustic wave processing apparatus according to (1), wherein the setting changing unit changes the setting of at least one of the transmitting unit, the receiving unit, the data processing unit, the image generation unit, and the display control unit on the basis of setting information on the data processing unit which is held in the setting information holding unit.

(3) The acoustic wave processing apparatus according to (1) or (2), wherein the setting changing unit changes the setting of the data processing unit on the basis of the setting information held in the setting information holding unit.

(4) The acoustic wave processing apparatus according to (1) to (3), wherein the data processing unit selects two or more pieces of first element data from among the plurality of pieces of first element data, and superimposes the selected two or more pieces of first element data in accordance with reception times at which the elements receive the acoustic wave echo and positions of the elements to generate second element data.

(5) The acoustic wave processing apparatus according to (1) to (3), further including a phasing addition unit that performs phasing addition on each of the pieces of first element data by using at least two elements as references to generate at least two pieces of first reception data for each of the pieces of first element data, wherein the data processing unit selects two or more pieces of first reception data from among the plurality of pieces of first reception data, and superimposes the selected two or more pieces of first reception data in accordance with reception times at which the elements receive the acoustic wave echo to generate second reception data.

(6) The acoustic wave processing apparatus according to (5), wherein the data processing unit superimposes the two or more pieces of first reception data, the two or more pieces of first reception data being generated from the pieces of first element data, which are different from each other, from the plurality of pieces of first reception data and being generated by subjecting the different pieces of first element data to phasing addition processing by using an identical element as a reference.

(7) The acoustic wave processing apparatus according to any of (1) to (6) wherein setting information in the data processing unit is information on at least one of the number of pieces of data to be superimposed, apodization, sound velocity, and delay time.

(8) The acoustic wave processing apparatus according to any of (1) to (7), wherein the change of the measurement condition is changing a probe including the probe unit.

(9) The acoustic wave processing apparatus according to any of (1) to (8), wherein the change of the measurement condition is changing the transmit focal point of the acoustic wave beam transmitted by the transmitting unit.

(10) The acoustic wave processing apparatus according to any of (1) to (9), wherein the setting information on the image generation unit is a gain value for amplifying the processed data, and the setting changing unit changes setting of the gain value on the basis of information on the number of pieces of data to be superimposed in the data processing unit.

(11) The acoustic wave processing apparatus according to any of (1) to (10), wherein the transmitting unit causes the probe unit to transmit the acoustic wave beam the plurality of times by at least either changing an element serving as a center or changing a transmit direction of the acoustic wave beam.

(12) A signal processing method for an acoustic wave processing apparatus for examining an inspection object by using a probe unit having a plurality of elements arranged therein, the probe unit being configured to transmit an acoustic wave beam, receive an acoustic wave echo reflected by the inspection object, and output an analog element signal corresponding to the received acoustic wave echo, the signal processing method including:

a transmitting step of performing a plurality of times an operation of transmitting the acoustic wave beam by using two or more elements among the plurality of elements of the probe unit as transmit elements so as to form a predetermined transmit focal point;

a receiving step of receiving an acoustic echo corresponding to each transmission of the acoustic beam with two or more elements among the plurality of elements as reception elements, receives analog element signals output from the reception elements, and performing predetermined processing on the analog element signals;

an A/D conversion step of performing A/D conversion on the analog element signals processed in the receiving step to convert the analog element signals to first element data as a digital element signal;

a data processing step of selecting two or more pieces of data from among a plurality of pieces of the first element data output in the A/D conversion step or from among a plurality of pieces of first reception data generated by performing phasing addition processing on the first element data, and performing superimposition processing to generate processed data;

an image generating step of generating an acoustic wave image on the basis of the processed data generated in the data processing step;

a display control step of causing a display unit to display the generated acoustic wave image;

a setting information holding step of holding setting information on at least one of the transmitting step, the receiving step, the data processing step, the image generating step, and the display control step; and a setting information changing step of, in a case where a measurement condition is changed, changing setting of at least one of the transmitting step, the receiving step, the data processing step, the image generating step, and the display control step on the basis of the setting information held in the setting information holding step, the setting being related to the acoustic wave image generated on the basis of the processed data.

(13) A non-transitory computer readable recording medium storing a signal processing program for an acoustic wave processing apparatus, the signal processing program being a program for causing a computer to execute a signal processing method for the acoustic wave processing apparatus for examining an inspection object by using a probe unit having a plurality of elements arranged therein, the probe unit being configured to transmit an acoustic wave beam, receive an acoustic wave echo reflected by the inspection object, and output an analog element signal corresponding to the received acoustic wave echo, the signal processing program causing the computer to execute:

a transmitting step of performing a plurality of times an operation of transmitting the acoustic wave beam by using two or more elements among the plurality of elements of the probe unit as transmit elements so as to form a predetermined transmit focal point;

a receiving step of receiving an acoustic echo corresponding to each transmission of the acoustic beam with two or more elements among the plurality of elements as reception elements, receiving analog element signals output from the reception elements, and performing predetermined processing on the analog element signals;

an A/D conversion step of performing A/D conversion on the analog element signals processed in the receiving step to convert the analog element signals to first element data as a digital element signal;

a data processing step of selecting two or more pieces of data from among a plurality of pieces of the first element data output in the A/D conversion step or from among a plurality of pieces of first reception data generated by performing phasing addition processing on the first element data, and performing superimposition processing to generate processed data;

an image generating step of generating an acoustic wave image on the basis of the processed data generated in the data processing step;

a display control step of causing a display unit to display the generated acoustic wave image;

a setting information holding step of holding setting information on at least one of the transmitting step, the receiving step, the data processing step, the image generating step, and the display control step; and a setting information changing step of, in a case where a measurement condition is changed, changing setting of at least one of the transmitting step, the receiving step, the data processing step, the image generating step, and the display control step on the basis of the setting information held in the setting information holding step, the setting being related to the acoustic wave image generated on the basis of the processed data.

According to an aspect of the present invention, it is possible to provide an acoustic wave processing apparatus, a signal processing method, and a non-transitory computer readable recording medium storing a program that can prevent, if a probe or a transmit condition is changed in an acoustic wave processing apparatus which performs multi-line processing, a large change in image lightness or frame rate before and after the change.

BRIEF DESCRIPTION OF THE DRAWINGS

FIG. 4A and FIG. 4C are each a conceptual diagram for describing transmission and reception of ultrasonic waves by using an ideal ultrasonic beam, and FIG. 4B and FIG. 4D are conceptual diagrams illustrating element data obtained by each transmission and reception of ultrasonic waves;

FIG. 5A and FIG. 5C are each a conceptual diagram for describing transmission and reception of ultrasonic waves by using an actual ultrasonic beam, and FIG. 5B and FIG. 5D are conceptual diagrams illustrating element data obtained by each transmission and reception of ultrasonic waves;

Figure 1:
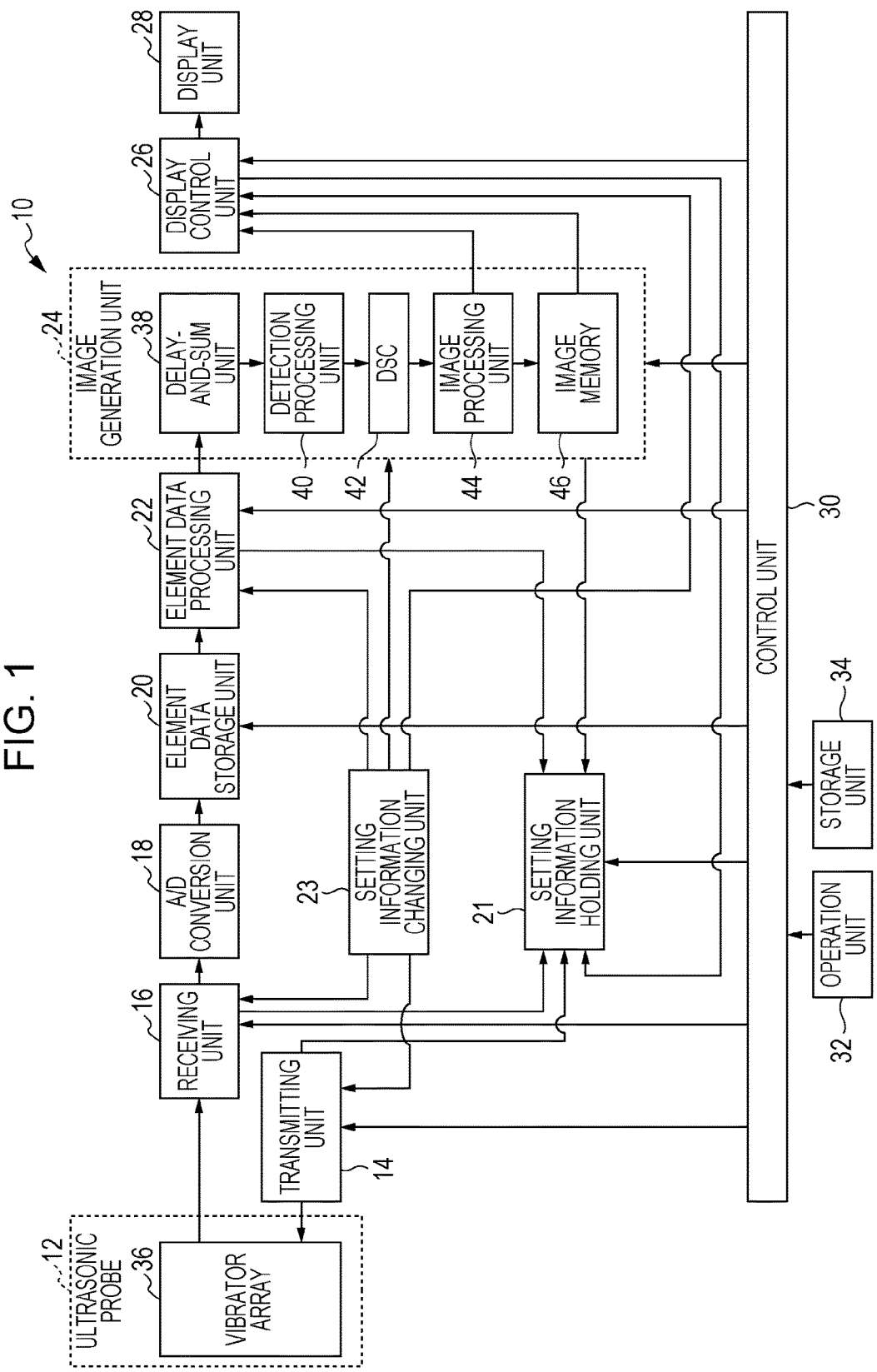
FIG. 1 is a block diagram conceptually illustrating an example of the configuration of an ultrasonic diagnostic apparatus of the present invention.
Figure 7:
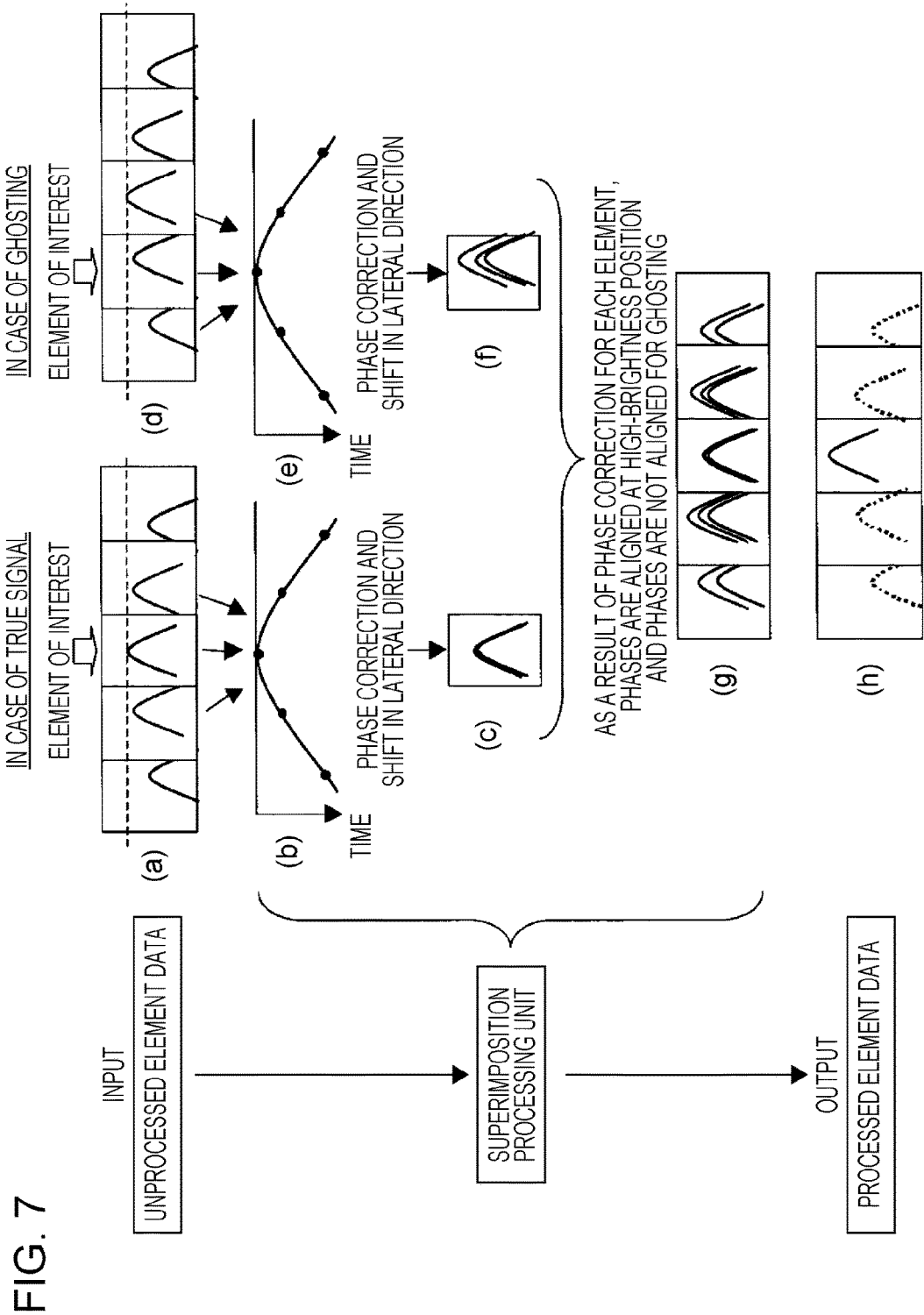
Figure 8:
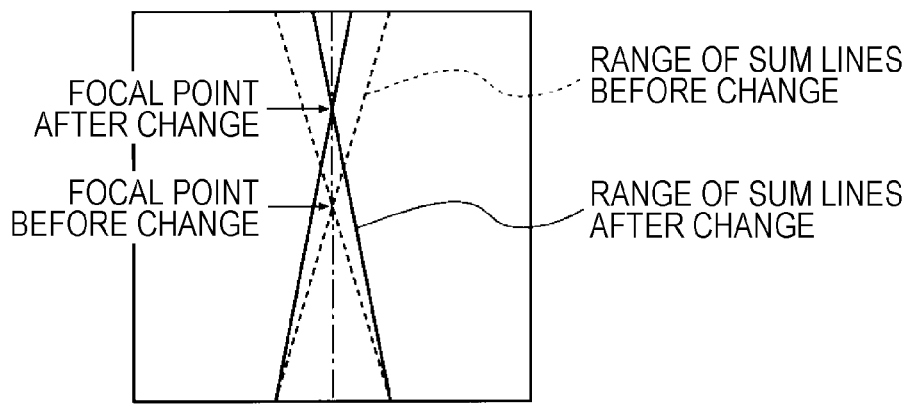
Figure 9A:
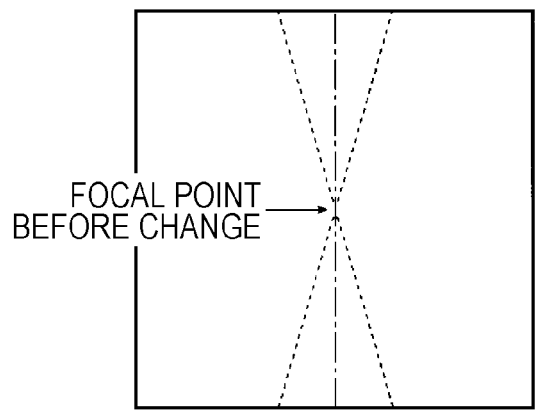
Figure 9B:
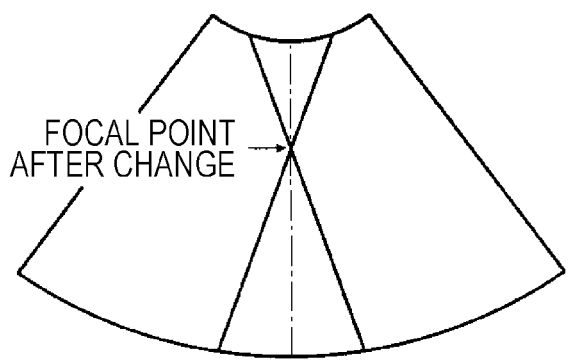
Figure 10A:
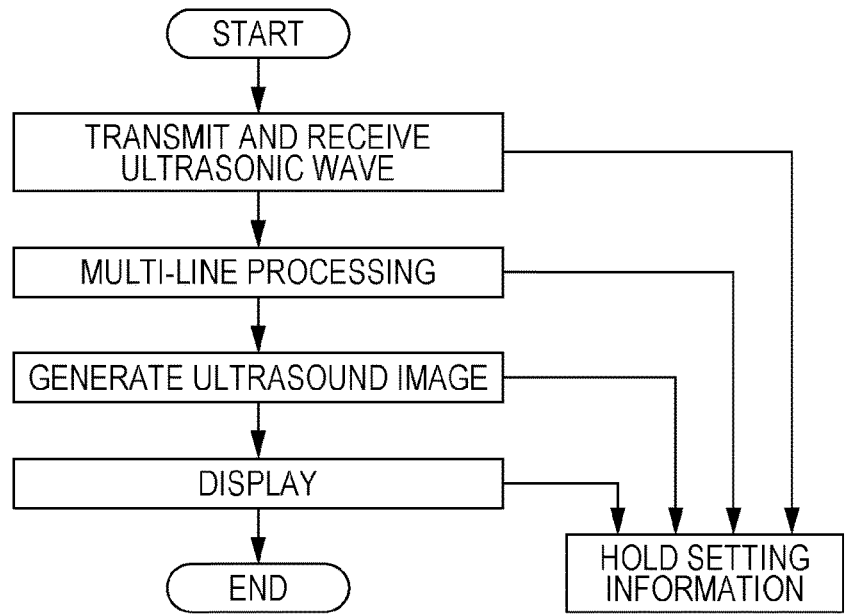
Figure 10B:
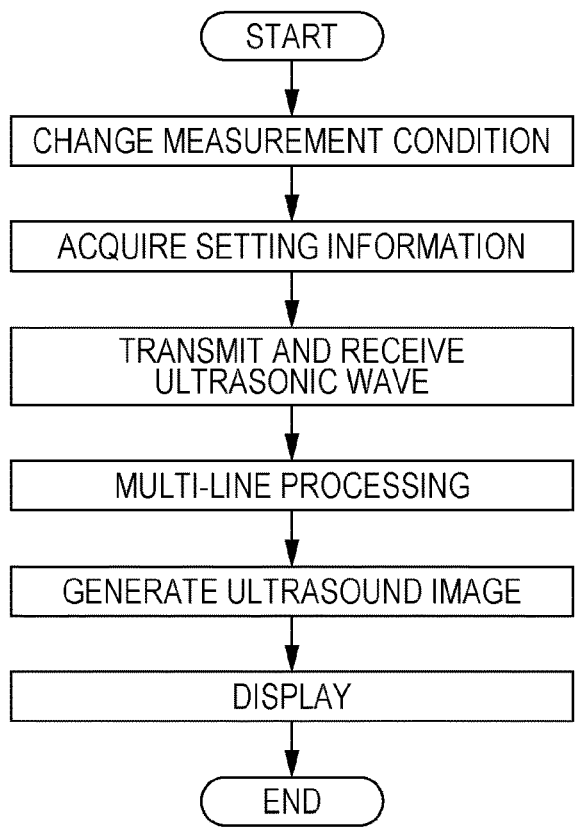
Figure 11:
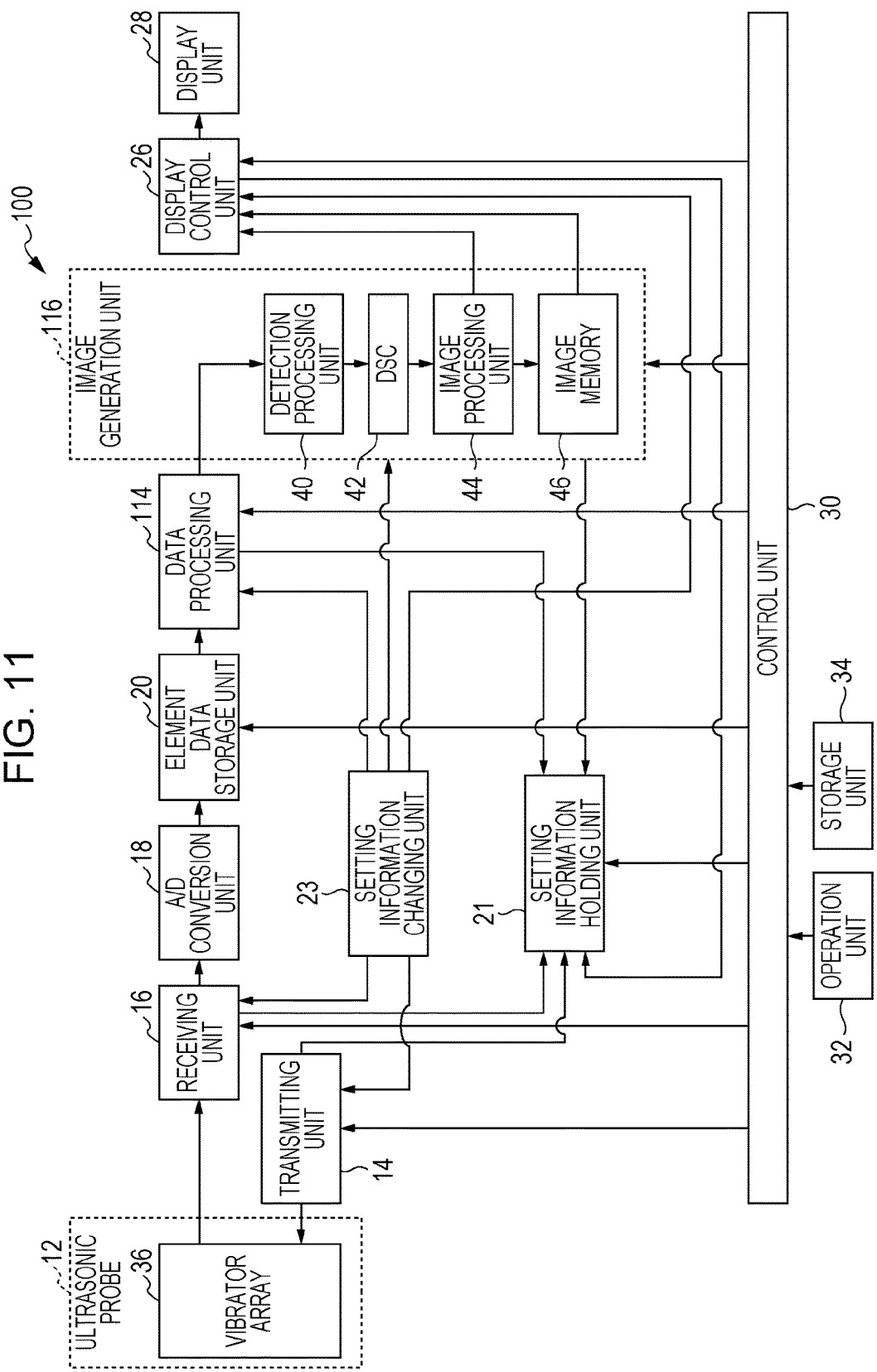
Figure 12:
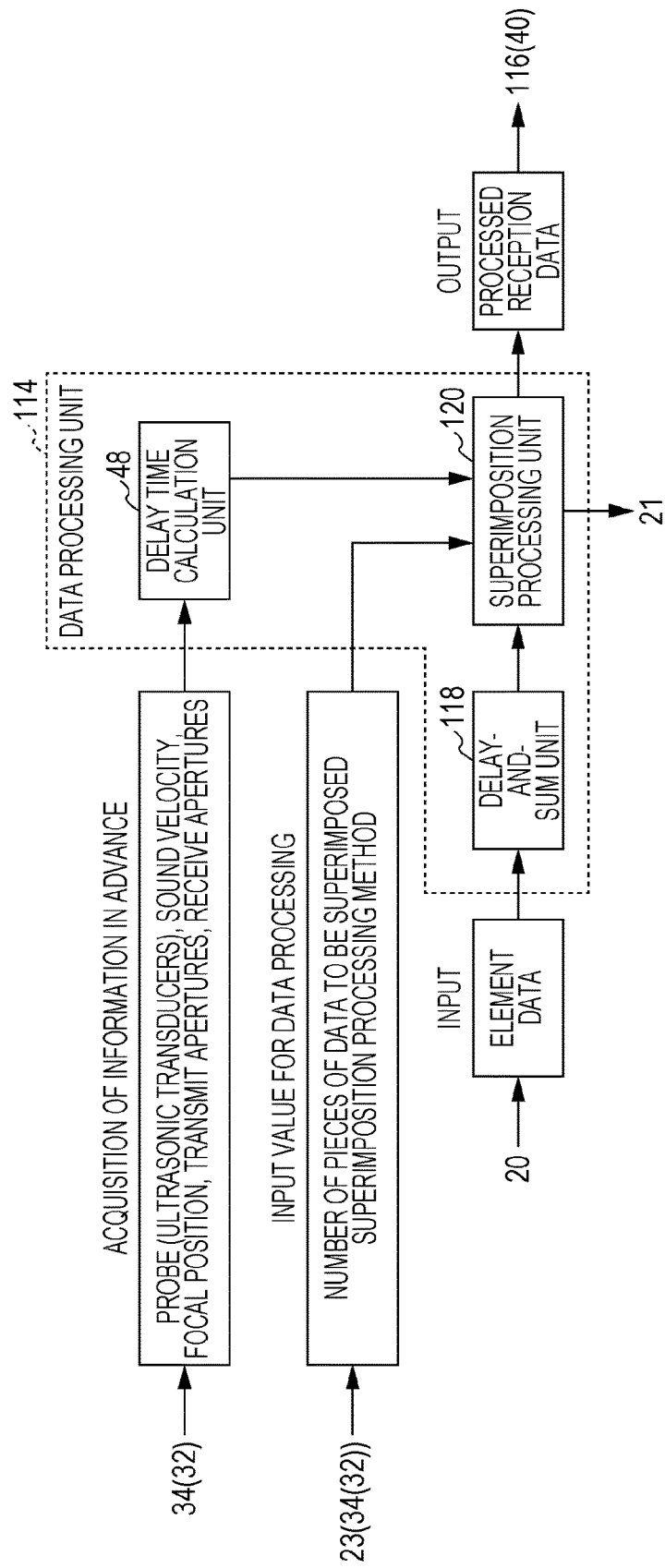
Figure 13:
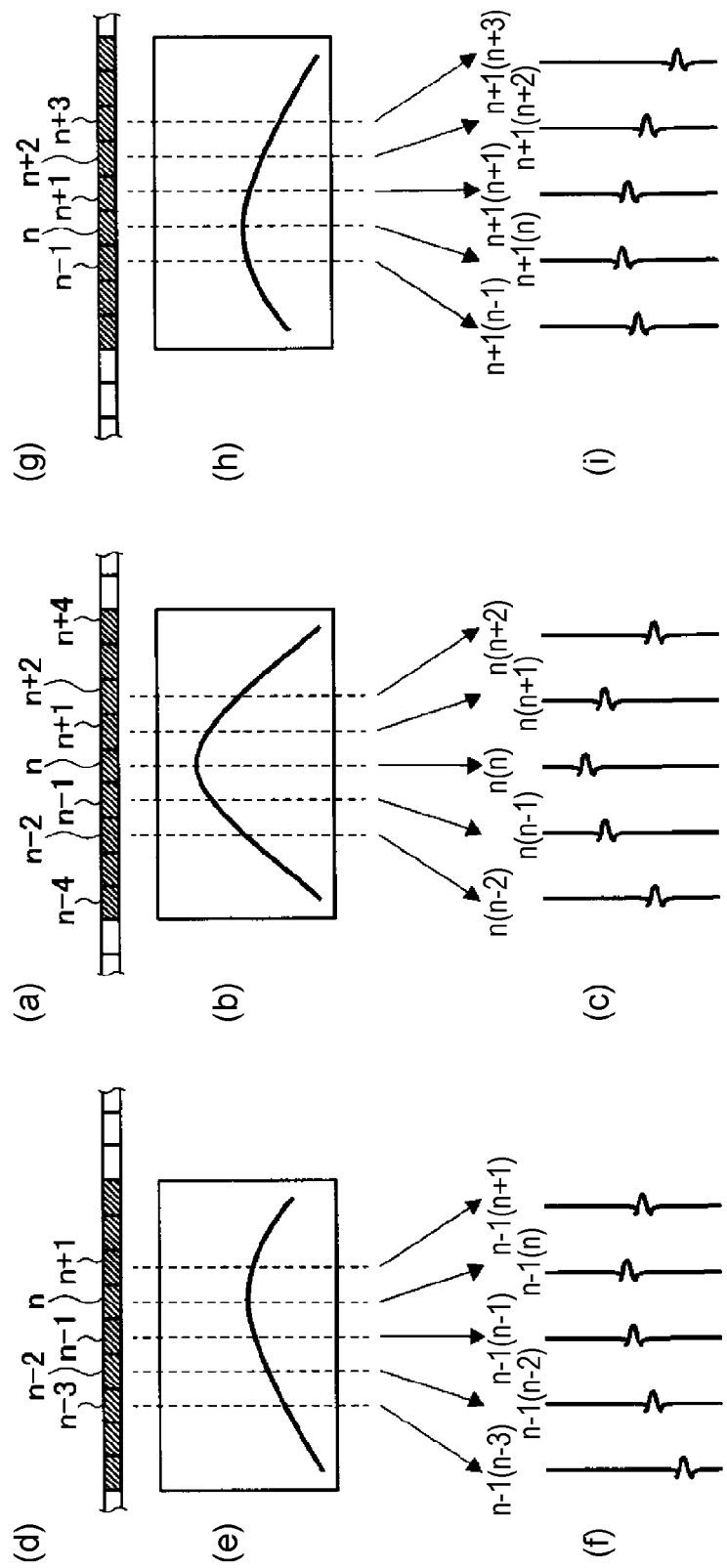
Figure 14:
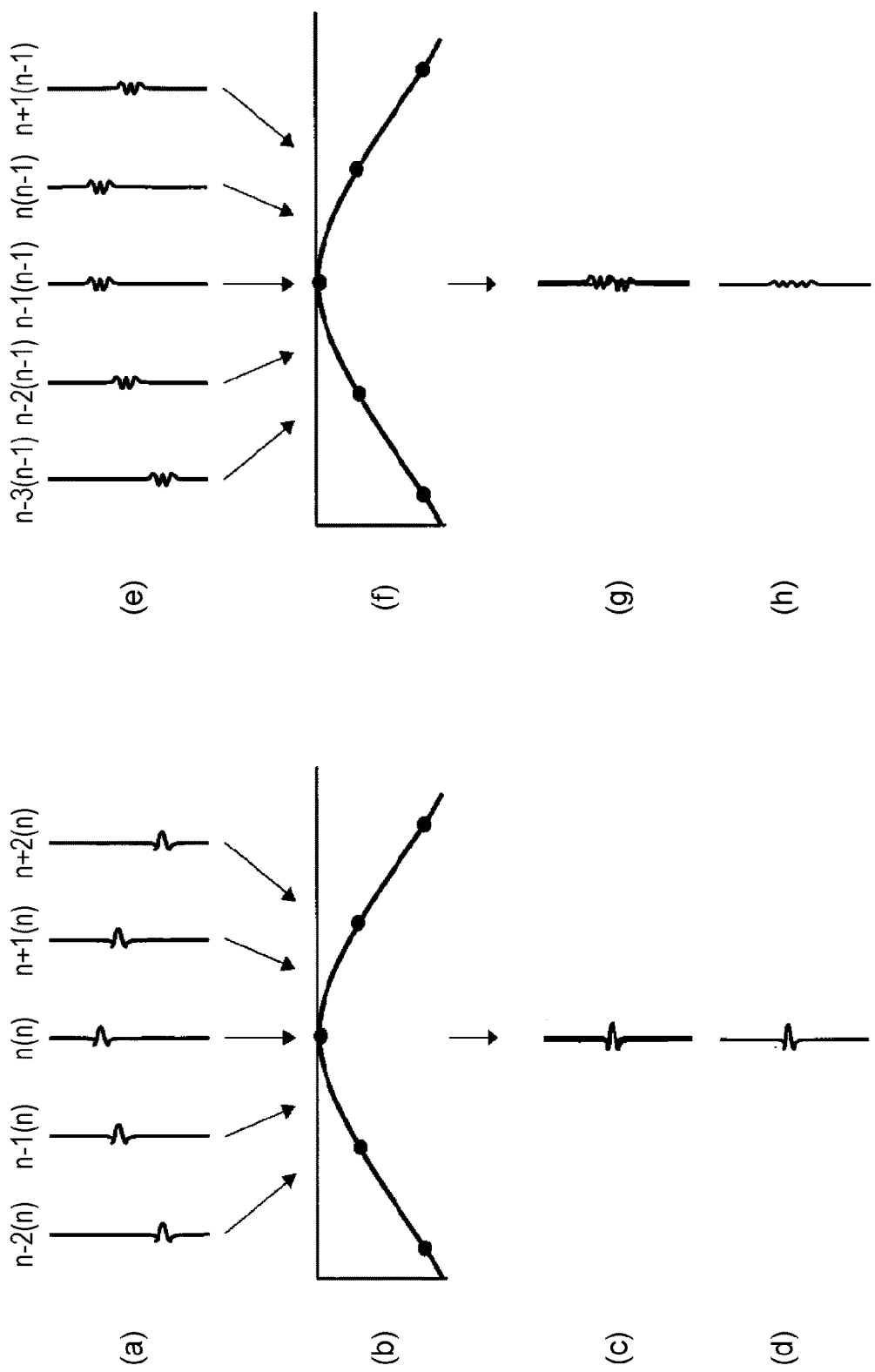

Parts (a), (b), and (c) of FIG. 7 are conceptual diagrams for respectively describing element data of a true signal, their delay times, and the state of superimposed element data, parts (d), (e), and (f) of FIG. 7 are conceptual diagrams for respectively describing element data for ghosting, their delay times, and the state of superimposed element data, part (g) of FIG. 7 is a conceptual diagram for describing states of superimposed element data corresponding to a plurality of elements, and part (h) of FIG. 7 is a conceptual diagram for describing the result of superimposition of the element data in part (g) of FIG. 7;

FIG. 8 is a conceptual diagram for describing an example of a change of setting information;

FIG. 9A and FIG. 9B are conceptual diagrams for describing another example of the change of the setting information;

FIG. 10A and FIG. 10B are flowcharts for describing an operation of the ultrasonic diagnostic apparatus illustrated in FIG. 1;

FIG. 11 is a block diagram conceptually illustrating another example of the configuration of the ultrasonic diagnostic apparatus of the present invention;

FIG. 12 is a block diagram conceptually illustrating an example of the configuration of a data processing unit of the ultrasonic diagnostic apparatus illustrated in FIG. 11;

Parts (a), (d), and (g) of FIG. 13 are conceptual diagrams for describing individual receive elements, parts (b), (e), and (h) of FIG. 13 are conceptual diagrams illustrating element data obtained by each transmission and reception of ultrasonic waves, and parts (c), (f), and (i) of FIG. 13 are conceptual diagrams illustrating unprocessed reception data obtained by subjecting individual pieces of element data to phasing addition processing; and Parts (a) and (e) of FIG. 14 are each a conceptual diagram illustrating unprocessed reception data to be subjected to superimposition, parts (b) and (f) of FIG. 14 are conceptual diagrams for describing their delay times, parts (c) and (g) of FIG. 14 are conceptual diagrams for describing the state of superimposed unprocessed reception data, and parts (d) and (h) of FIG. 14 are conceptual diagrams for describing the result of superimposition of the unprocessed reception data.

DESCRIPTION OF THE PREFERRED EMBODIMENTS

An acoustic wave processing apparatus, a signal processing method, and a non-transitory computer readable recording medium storing a program of the present invention will be described in detail hereinafter based on a preferred first embodiment illustrated in the accompanying drawings.

While an ultrasonic wave is employed as an acoustic wave in embodiments of the present invention, the acoustic wave is not limited to an ultrasonic wave and an acoustic wave having an audible frequency may be used as long as an appropriate frequency is selected in accordance with the examination target, the measurement conditions, and so on.

FIG. 1 conceptually illustrates in block diagram form an example of an ultrasonic diagnostic apparatus (acoustic wave processing apparatus) of the present invention.

As illustrated in FIG. 1, an ultrasonic diagnostic apparatus 10 includes an ultrasonic probe 12, a transmitting unit 14 and a receiving unit 16, which are connected to the ultrasonic probe 12, an A/D conversion unit 18, an element data storage unit 20, a setting information holding unit 21, an element data processing unit 22, a setting changing unit 23, an image generation unit 24, a display control unit 26, a display unit 28, a control unit 30, an operation unit 32, and a storage unit 34.

In the illustrated example, the transmitting unit 14, the receiving unit 16, the A/D conversion unit 18, the element data storage unit 20, the setting information holding unit 21, the element data processing unit 22, the setting changing unit 23, the image generation unit 24, the display control unit 26, the display unit 28, the control unit 30, the operation unit 32, and the storage unit 34 constitute an apparatus body of the ultrasonic diagnostic apparatus 10.

The apparatus body and the ultrasonic probe 12 are configured to be removable from each other, and a variety of ultrasonic probes such as a linear probe and a convex probe are attachable to the apparatus body.

The ultrasonic diagnostic apparatus 10 of the present invention is configured such that at least one of the pieces of setting information in the transmitting unit 14, the receiving unit 16, the element data processing unit 22, the image generation unit 24, and the display control unit 26 is held in the setting information holding unit 21 and, if a measurement condition is changed, the setting changing unit 23 changes the setting of at least one of the transmitting unit 14, the receiving unit 16, the element data processing unit 22, the image generation unit 24, and the display control unit 26 on the basis of the setting information held in the setting information holding unit 21.

Here, the term change of a measurement condition, as used in the present invention, refers to at least one of a change of a transmit condition of an ultrasonic beam in the transmitting unit 14, a change of a receive condition of an ultrasonic echo in the receiving unit 16, a change of the ultrasonic probe 12, a change in frame rate, and a change of the measurement mode.

Specifically, transmit conditions as measurement conditions include the number of transmit apertures, the position of the transmit focal point, the F value, the number of transmissions, and the transmit frequency. Further, receive conditions include the number of receive apertures, the number of receptions, and the sampling frequency.

In addition, the change of the ultrasonic probe involves changing the ultrasonic probe to a different type of probe, such as a linear probe or a convex probe, or to a probe having a different spacing, a different shape, or the like of each ultrasonic transducer (element).

In addition, the change of the measurement mode involves changing a mode for the transmission and reception of an ultrasonic wave during measurement. Examples of the measurement mode include a fundamental mode for generating an ultrasound image on the basis of the fundamental component of a received ultrasonic echo, a THI mode for generating an ultrasound image on the basis of the harmonic component of a received ultrasonic echo, a spatial compounding mode for combining a plurality of ultrasound images obtained by transmission and reception of ultrasonic waves in different directions to generate a composite image, and a frequency compounding mode for combining a plurality of ultrasound images obtained from ultrasonic waves having different frequencies to generate a composite image.

The individual components constituting the ultrasonic diagnostic apparatus 10 of the present invention will be described hereinafter.

The ultrasonic probe (ultrasonic probe unit) 12 is a well-known ultrasonic probe used in a typical ultrasonic diagnostic apparatus.

The ultrasonic probe 12 (hereinafter referred to as the probe 12) includes a vibrator array 36 configured such that ultrasonic transducers are arranged one-dimensionally or two-dimensionally.

When imaging an ultrasound image of an inspection object (hereinafter referred to as a subject), the ultrasonic transducers transmit ultrasonic beams to the subject in accordance with respective drive signals supplied from the transmitting unit 14, and, in addition, receive ultrasonic echoes reflected by the subject and output reception signals corresponding to the intensities of the received ultrasonic waves.

Each of the ultrasonic transducers is constituted by a vibrator having an electrode at either end of a piezoelectric body composed of, for example, a piezoelectric ceramic such as PZT (lead zirconate titanate), a polymer piezoelectric element such as that made of PVDF (polyvinylidene fluoride), or a piezoelectric single crystal such as PMN-PT (lead magnesium niobate-lead titanate solid solution).

When a pulsed or continuous-wave voltage is applied to the electrodes of the vibrator, the piezoelectric body expands and contracts in accordance with the applied voltage, causing a pulsed or continuous-wave ultrasonic wave to emanate from each vibrator. The ultrasonic waves emanating from the respective vibrators converge to a set focal point and are combined (that is, transmit-focused) in accordance with the respective driving delays of the vibrators to thereby form an ultrasonic beam.

In addition, the vibrators expand and contract in response to incoming ultrasonic echoes which are reflected within the subject, and produce electrical signals in accordance with the magnitude of the expansion and contraction. The electrical signals are output to the receiving unit 16 as reception signals (analog element signals).

The transmitting unit 14 includes a plurality of pulsers, for example, and supplies drive signals (applies drive voltages) to the respective ultrasonic transducers (vibrators) of the probe 12.

The transmitting unit 14 performs transmit-focusing for adjusting amounts of delay of the drive signals (the application timings of the drive voltages) on the basis of transmit delay patterns selected by the control unit 30 so as to form an ultrasonic beam in such a manner that ultrasonic waves transmitted from a predetermined number of (a plurality of) ultrasonic transducers at predetermined transmit frequencies converge to a set focal point, and supplies the drive signals to the ultrasonic transducers.

Thus, an intended ultrasonic beam is transmitted to the subject from the probe 12 (the vibrator array 36).

In accordance with a control signal from the control unit 30, the receiving unit 16 receives reception signals output from the predetermined number of (the plurality of) ultrasonic transducers at predetermined sampling frequencies in response to a single transmission of an ultrasonic beam, performs predetermined processing such as amplification or amplification (so-called STC) corresponding to a time of reception (depth), and supplies the resulting signals to the A/D conversion unit 18.

Note that, in the ultrasonic diagnostic apparatus 10 of the present invention, the method for transmission and reception of an ultrasonic wave is basically similar to that in a well-known ultrasonic diagnostic apparatus.

Thus, in a single transmission and reception of ultrasonic waves (transmission of a single ultrasonic beam and reception of an ultrasonic echo in response to this transmission), there is no limitation on the number of ultrasonic transducers (the number of transmit apertures) that produce ultrasonic waves or the number of ultrasonic transducers (the number of receive apertures) that receive ultrasonic waves (from which the receiving unit 16 receives reception signals) as long as the numbers are both plural. In a single transmission and reception, furthermore, the numbers of apertures for transmission and reception may be the same or different.

In addition, there is also no limitation on the number of transmissions and receptions of ultrasonic waves (the number of sound rays) for forming a single ultrasound image or the spacing of an ultrasonic transducer (central element) on which transmission and reception are centered (that is, the density of scan lines/sound rays) as long as ultrasonic beams adjacent in at least the azimuth direction (the arrangement direction of the ultrasonic transducers) have overlapping transmit areas. Thus, transmission and reception of ultrasonic waves may be performed by using as central elements all the ultrasonic transducers corresponding to an area scanned with ultrasonic waves, or transmission and reception of ultrasonic waves may be performed by using as central elements ultrasonic transducers spaced apart at predetermined intervals such as every two or four transducers.

Furthermore, in a manner similar to that in a well-known ultrasonic diagnostic apparatus, transmission and reception are performed at a plurality of positions (lines) with the sequential movement of transmit and receive positions to form a single ultrasound image.

Here, the transmitting unit 14 and the receiving unit 16 supply setting information obtained in a case where transmission and reception of an ultrasonic wave is performed to the setting information holding unit 21. In addition, if any instructions are given from the setting changing unit 23 to change the setting information in accordance with a change of the ultrasonic probe 12 and/or a change of a transmit condition, that is, a change of a measurement condition, the transmitting unit 14 and the receiving unit 16 change a condition for transmission and reception on the basis of setting information from the setting changing unit 23.

The change of the setting information will be described in detail below.

Note that, if a transmit condition for the transmitting unit 14 is changed as a change of a measurement condition, the setting changing unit 23 changes setting information other than the setting of the transmitting unit 14 that has been changed as a measurement condition.

Also, if a transmit condition for the receiving unit 16 is changed as a change of a measurement condition, the setting changing unit 23 changes setting information other than the setting of the receiving unit 16 that has been changed as a measurement condition.

Here, the term setting information on the transmitting unit 14 refers to information such as the position of the transmit focal point, the F value, the number of transmit apertures, the transmit frequency, or the number of transmissions per frame.

Further, the term setting information on the receiving unit 16 refers to information such as the number of receive apertures, the degree of amplification (gain), the degree of amplification based on STC (STC gain), the number of receptions per frame, or the sampling frequency.

The A/D conversion unit 18 performs analog/digital conversion on the analog reception signals supplied from the receiving unit 16 into element data (first element data) that is digital reception signals.

The A/D conversion unit 18 supplies the element data subjected to A/D conversion to the element data storage unit 20.

The element data storage unit 20 sequentially stores the element data supplied from the A/D conversion unit 18. The element data storage unit 20 further stores information related to the frame rate (for example, parameters indicating the depth of the reflection position of the ultrasonic wave, the density of the scan lines, and the width of the field of view), which is input from the control unit 30, in association with each piece of element data.

Preferably, the element data storage unit 20 stores all pieces of element data corresponding to at least one ultrasound image (an ultrasound image of one frame) and does not delete the element data of the ultrasound image currently being displayed or an ultrasound image yet to be displayed at least until the display of the ultrasound image is completed.

The element data processing unit 22 is a part that superimposes element data to generate processed element data (second element data) corresponding to each piece of element data.

Specifically, the element data processing unit 22 superimposes, among the pieces of element data stored in the element data storage unit 20, pieces of element data obtained by transmitting a predetermined number of (a plurality of) ultrasonic beams for which the ultrasonic transducers serving as the centers (the elements serving as the centers (central elements)) are different and which have overlapping transmit areas, on the basis of the control by the control unit 30 and setting information from the setting changing unit 23, in accordance with the times at which the respective ultrasonic transducers receive the ultrasonic echoes (the delay times) and the positions of the ultrasonic transducers, thereby generating processed element data corresponding to element data (element data of an element of interest described below).

The process performed in the element data processing unit 22 will be described in detail below.

Here, the element data processing unit 22 supplies to the setting information holding unit 21 setting information with which element data is processed. In addition, if instructions are given from the setting changing unit 23 to change the setting information in response to a change of a measurement condition, the element data processing unit 22 changes a processing condition of element data on the basis of the setting information from the setting changing unit 23.

The term setting information on the element data processing unit 22 refers to information such as the number of superimpositions of element data, a weighting factor for superimposition (an apodization factor), a delay time used for superimposition, and a sound velocity for calculating a delay time.

The change of the setting information will be described in detail below.

The element data processing unit 22 delivers the generated processed element data to the image generation unit 24.

The image generation unit 24 is configured to generate reception data (sound ray signals) from the processed element data supplied from the element data processing unit 22 on the basis of the control by the control unit 30 and to generate an ultrasound image from the reception data.

The image generation unit 24 includes a phasing addition unit 38, a detection processing unit 40, a DSC 42, an image processing unit 44, and an image memory 46.

Note that the image generation unit 24 may also include an amplifier that amplifies a signal, and so on in addition to the parts described above.

The phasing addition unit 38 executes phasing addition on the processed element data generated by the element data processing unit 22 to perform a receive-focusing process, and generates reception data.

As described above, the vibrator array 36 of the probe 12 is configured such that a plurality of elements (ultrasonic transducers) are arranged one-dimensionally or two-dimensionally. Thus, the distance to a single reflection point in the subject differs from one ultrasonic transducer to another. This causes even ultrasonic echoes reflected at the same reflection point to arrive at the individual ultrasonic transducers at different times. The phasing addition unit 38 delays each signal of the processed element data by an amount corresponding to an arrival time difference (delay time) of the ultrasonic echo for each ultrasonic transducer in accordance with a receive delay pattern selected by the control unit 30, and executes phasing addition on the processed element data to which the respective delay times are applied to perform a receive-focusing process digitally, thereby generating reception data.

The phasing addition unit 38 supplies the generated reception data to the detection processing unit 40.

Figure 2:
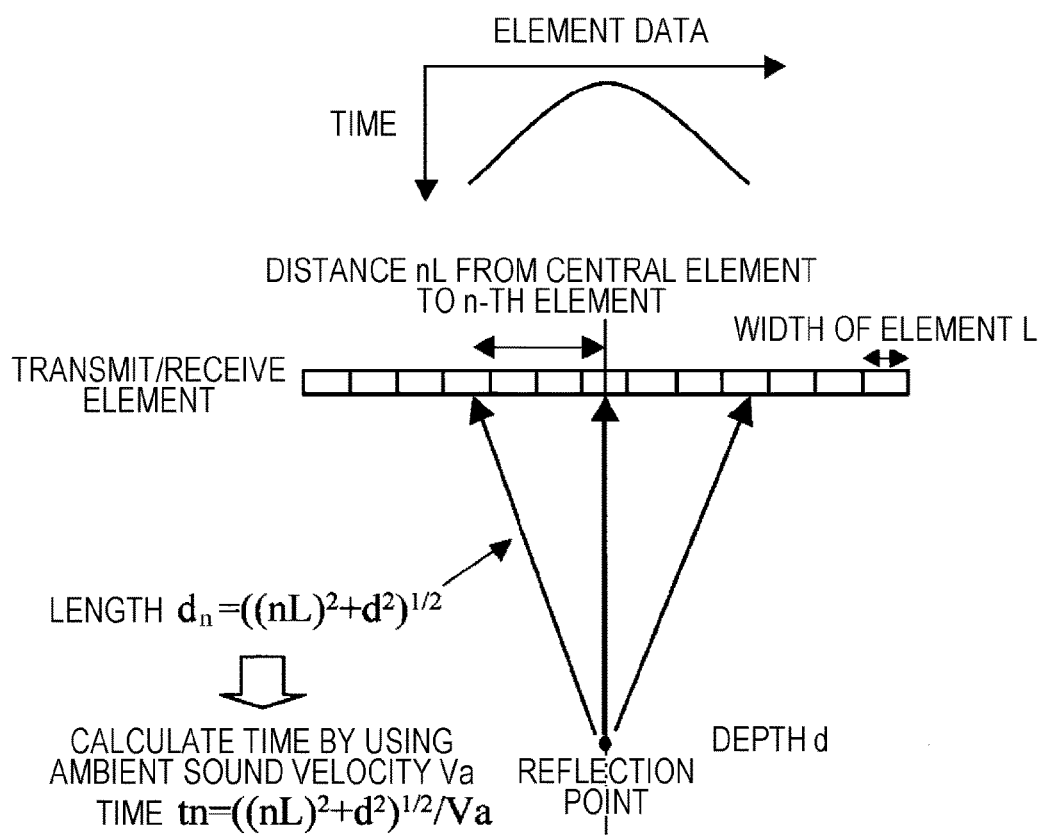
FIG. 2 is a conceptual diagram for describing an example of a receive-focusing process in the ultrasonic diagnostic apparatus illustrated in FIG. 1.

FIG. 2 illustrates an example of the receive-focusing process.

Here, FIG. 2 depicts the case of a linear probe in which the plurality of ultrasonic transducers of the probe 12 are arranged in a line in the horizontal direction in the diagram. The same concept may apply to a convex probe although it has a different probe shape.

Letting the width of each ultrasonic transducer in the azimuth direction be L, the distance from the central ultrasonic transducer in the azimuth direction to the n-th ultrasonic transducer toward the end position is given by nL.

It is assumed that, as illustrated in the same diagram, the reflection point of the ultrasonic wave is located at a distance (depth) d, which is vertical to the arrangement direction, from the central ultrasonic transducer. Then, the distance (length) $d_n$ between the n-th ultrasonic transducer and the reflection point is calculated in accordance with Equation (1).

$$d_n=((nL)^2+d^2)^{1/2} \quad (1)$$

Thus, the time $t_n$ taken for the ultrasonic echo from the reflection point to arrive at (to be received by) the n-th ultrasonic transducer is calculated in accordance with Equation (2) by using the sound velocity (ambient sound velocity) Va of the ultrasonic wave in the subject.

$$t_n=d_n/Va=((nL)^2+d^2)^{1/2}/Va \quad (2)$$

As described above, the distances between the ultrasonic transducers and the reflection point differ from ultrasonic transducer to ultrasonic transducer. In this example, therefore, as illustrated in the graph at the top of the diagram, the closer the ultrasonic transducer to the end position in the arrangement direction, the longer the arrival time $t_n$ of the ultrasonic echo.

Specifically, if the time taken for the ultrasonic wave from the reflection point to be received by the central ultrasonic transducer is denoted by $t_1$, the ultrasonic wave received by the n-th ultrasonic transducer is delayed by the time $\Delta t=t_n-t_1$ with respect to the ultrasonic wave received by the central ultrasonic transducer. In this example, the delay time $\Delta t$ corresponds to a receive delay pattern.

The phasing addition unit 38 executes phasing addition on the signals corresponding to the respective ultrasonic transducers by using the delay times represented by the time $\Delta t$ described above to perform a receive-focusing process, and generates reception data.

The detection processing unit 40 corrects the reception data generated by the phasing addition unit 38 for attenuation caused by the distance in accordance with the depth of the reflection position of the ultrasonic wave. Specifically, the detection processing unit 40 performs reception data amplification on the reception data by using the degree of amplification (gain) corresponding to the depth. Note that, in the following description, amplification of reception data in accordance with the depth is also referred to as STC and the degree of amplification for each depth during STC is also referred to as STC gain.

After amplifying the reception data in accordance with the depth, the detection processing unit 40 performs envelope detection processing to generate B-mode image data that is tomographic image information (brightness image information) in the subject.

The DSC (digital scan converter) 42 converts (raster-converts) the B-mode image data generated by the detection processing unit 40 into image data that supports a normal television signal scanning system.

The image processing unit 44 performs various kinds of necessary image processing, such as gradation processing, on the B-mode image data input from the DSC 42 to produce B-mode image data for display. The image processing unit 44 outputs the B-mode image data subjected to the image processing to the display control unit 26 for display and/or stores the B-mode image data subjected to the image processing in the image memory 46.

The image memory 46 is a well-known storage means (storage medium) that stores the B-mode image data processed by the image processing unit 44. The B-mode image data stored in the image memory 46 is read by the display control unit 26 for display by using the display unit 28, as necessary.

Here, the image generation unit 24 supplies to the setting information holding unit 21 setting information with which an ultrasound image is generated. In addition, if instructions are given from the setting changing unit 23 to change the setting information in response to a change of a measurement condition, the image generation unit 24 changes a processing condition for image generation on the basis of the setting information from the setting changing unit 23.

Note that the term setting information in the image generation unit 24 refers to setting information such as the degree of amplification (STC gain) corresponding to the depth or gain in the detection processing unit 40, or image processing parameters in the image processing unit 44.

Here, the term image processing parameters are, for example, settings of a filter to perform smoothing processing on an image.

The change of the setting information will be described in detail below.

The display control unit 26 causes the display unit 28 to display an ultrasound image by using the B-mode image data subjected to predetermined image processing by the image processing unit 44.

The display unit 28 includes, for example, a display device such as an LCD, and displays an ultrasound image under control of the display control unit 26.

Here, the display control unit 26 supplies to the setting information holding unit 21 setting information for displaying an image. In addition, if instructions are given from the setting changing unit 23 to change the setting information in response to a change of a measurement condition, the display control unit 26 changes the settings for displaying an image on the basis of the setting information from the setting changing unit 23.

Note that the term setting information in the display control unit 26 refers to setting information such as the display size of the image or display setting.

Here, the term display setting refers to the setting of a display method such as the display of a created image alone, or synthetic display or simultaneous display of the created image and another mode of image.

The change of the setting information will be described in detail below.

The setting information holding unit 21 acquires and holds setting information on at least one of the transmitting unit 14, the receiving unit 16, the element data processing unit 22, the image generation unit 24, and the display control unit 26.

The setting information acquired by the setting information holding unit 21 is set in advance.

In addition, there is no particular limitation on the timing at which the setting information holding unit 21 acquires setting information on each component, and held setting information may be acquired at, for example, the point in time at which an examination starts (at which the transmission and reception of an ultrasonic wave start), or the point in time at which the setting is changed in response to an input operation given from the operation unit 32. Alternatively, setting information may be acquired every several frames or at predetermined time intervals.

Alternatively, if the setting of each component differs from one probe to another, the setting information holding unit 21 may acquire setting information when a probe is set and the setting of each component is changed. For example, the previous set values of the transmitting unit 14, the receiving unit 16, the element data processing unit 22, the image generation unit 24, and the display control unit 26 may be saved in the apparatus body for each probe. When a probe is set, the saved set values corresponding to the probe may be read and set and, in addition, the setting information holding unit 21 may acquire necessary setting information. In the configuration, furthermore, preset default values may be set for an initially connected probe.

If a measurement condition is changed, the setting information holding unit 21 supplies the setting information held therein to the setting changing unit 23.

The setting changing unit 23 is a part that, in a case where a measurement condition is changed, changes setting of at least one of the transmitting unit 14, the receiving unit 16, the element data processing unit 22, the image generation unit 24, and the display control unit 26 on the basis of the setting information held in the setting information holding unit 21, the setting being related to an acoustic wave image generated on the basis of processed element data generated by using multi-line processing.

This point will be described in detail below.

The setting changing unit 23 supplies the changed setting information to the respective components.

The control unit 30 is a part that controls each component of the ultrasonic diagnostic apparatus 10 in accordance with instructions input by an operator through the operation unit 32.

Further, the control unit 30 supplies various kinds of information input by the operator by using the operation unit 32 to a necessary part. For example, when information necessary to calculate a delay time, which is used in the element data processing unit 22 and the phasing addition unit 38 of the image generation unit 24, and information necessary for element data processing performed in the element data processing unit 22 are input to the operation unit 32, the control unit 30 supplies these pieces of information to the respective components, such as the transmitting unit 14, the receiving unit 16, the element data storage unit 20, the setting changing unit 23, the element data processing unit 22, the image generation unit 24 and the display control unit 26, as necessary.

In addition, if input is made from the operation unit 32 to change the setting of the transmitting unit 14, the receiving unit 16, the element data processing unit 22, the image generation unit 24, and the display control unit 26, the control unit 30 supplies to the setting information holding unit 21 information indicating that such input has been made.

In addition, if the setting of the transmitting unit 14 and/or the receiving unit 16 is changed and if the ultrasonic probe 12 is changed, that is, if a measurement condition is changed, the control unit 30 supplies to the setting changing unit 23 information indicating that the changes have been made.

The operation unit 32 is used by the operator to perform an input operation, and can be formed by a keyboard, a mouse, a trackball, a touch panel, or the like.

In addition, the operation unit 32 has an input function for allowing the operator to input various kinds of information, as necessary. For example, the operation unit 32 has an input function for inputting information on the probe 12 (the ultrasonic transducers), information related to the generation of processed element data, such as the transmit apertures and receive apertures in the probe 12 (the vibrator array 36), the number of pieces of element data to be superimposed, and the method for superimposing element data, the focal position of the ultrasonic beam, the gain in the receiving unit, the STC gain in the image generation unit 24, and so on.

The above input is made by, for example, the selection of a part to be imaged (a part to be diagnosed), the selection of image quality, the selection of the depth of the ultrasound image to be imaged, or the like.

The storage unit 34 is configured to store an operation program for allowing the control unit 30 to control each component of the ultrasonic diagnostic apparatus 10, transmit delay patterns, receive delay patterns, information related to the generation of processed element data, and information necessary for the control unit 30 to operate or control the ultrasonic diagnostic apparatus 10, such as information on the probe 12 and information on the transmit apertures, the receive apertures, and the focal position, which is input from the operation unit 32.

The storage unit 34 can be implemented using a well-known recording medium such as a hard disk, a flexible disk, an MO, an MT, a RAM, a CD-ROM, or a DVD-ROM.

Note that, in the ultrasonic diagnostic apparatus 10, the setting changing unit 23, the element data processing unit 22, the phasing addition unit 38, the detection processing unit 40, the DSC 42, the image processing unit 44, the display control unit 26, and so on are implemented by a CPU and an operation program for causing the CPU to perform various processing operations. In the present invention, however, these components may be implemented in digital circuitry.

As described above, the element data processing unit 22 is a part that superimposes, among the pieces of element data (unprocessed element data) stored in the element data storage unit 20, pieces of element data obtained by transmitting a predetermined number of (a plurality of) ultrasonic beams for which the ultrasonic transducers serving as the centers (central elements) are different and which have overlapping transmit areas, in accordance with the times at which the respective ultrasonic transducers perform reception and the positions of the ultrasonic transducers to generate processed element data.

Note that, in the following description, the ultrasonic transducers are also referred to simply as "elements".

Figure 3:
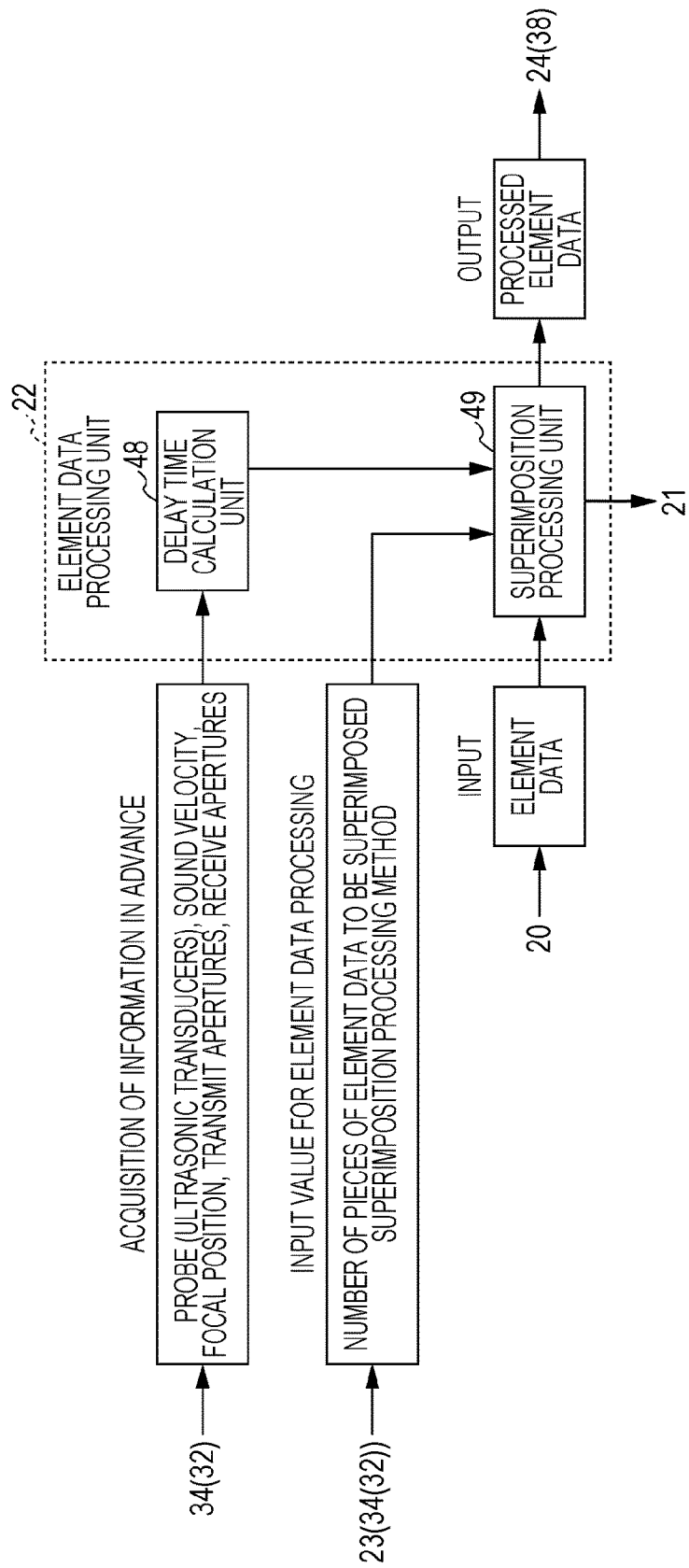
FIG. 3 is a block diagram conceptually illustrating an example of the configuration of an element data processing unit of the ultrasonic diagnostic apparatus illustrated in FIG. 1.

In FIG. 3, the configuration of the element data processing unit 22 is conceptually illustrated using a block diagram.

As illustrated in FIG. 3, the element data processing unit 22 includes a delay time calculation unit 48 and a superimposition processing unit 49.

The delay time calculation unit 48 acquires, in advance, information related to the probe 12 (the ultrasonic transducers (elements)), the focal position of the ultrasonic beam, the position of a sampling point (the output position of element data), the transmit apertures and receive apertures in the probe 12, and so on, which is input from the operation unit 32 or input from the operation unit 32 and stored in the storage unit 34.

Further, the delay time calculation unit 48 calculates the delay times of the ultrasonic echoes received by the elements in the receive apertures, that is, the delay times of the element data, on the basis of the geometric positions of the elements in the transmit apertures that oscillate ultrasonic waves to transmit (generate) an ultrasonic beam and the elements in the receive apertures that receive the ultrasonic echoes from the subject.

The delay time calculation unit 48 supplies information on the calculated delay times to the superimposition processing unit 49.

The superimposition processing unit 49 reads, from among the pieces of element data stored in the element data storage unit 20, pieces of element data to be subjected to superimposition (element data obtained by using ultrasonic beams for which the central elements are different and which have overlapping transmit areas (two or more pieces of element data generated for every two or more target regions)) on the basis of the information related to element data processing, such as the number of pieces of element data to be superimposed and the superimposition processing method, which is supplied from the condition changing unit 23, input from the operation unit 32, or input from the operation unit 32 and stored in the storage unit 34.

Further, the superimposition processing unit 49 superimposes the two or more pieces of element data in terms of reception time, that is, in such a manner that their times are aligned, and in such a manner that the received absolute positions of the elements of the probe unit are aligned, on the basis of the delay times corresponding to the respective pieces of element data, which are calculated by the delay time calculation unit 48, to generate processed element data.

The processing of element data, which is performed in the element data processing unit 22, will be described in detail hereinafter.

First, in a case where element data is obtained in the ultrasonic probe 12 by transmitting an ultrasonic beam to the subject from the transmit apertures, that is, elements (hereinafter referred to simply as transmit elements) that oscillate ultrasonic waves to transmit an ultrasonic beam, and by receiving an ultrasonic echo generated as a result of interaction with the subject by using the receive apertures, that is, elements (hereinafter referred to simply as receive elements) that receive ultrasonic echoes, the relationship between an ultrasonic beam from the transmit elements and element data obtained by the receive elements will be described.

As an example, as illustrated in FIG. 4A, an ultrasonic beam is transmitted by using three elements $52c$ to $52e$ as transmit elements, and an ultrasonic echo is received by using seven elements $52a$ to $52g$ as receive elements. Then, as illustrated in FIG. 4C, the elements are moved (hereinafter also referred to as shifted) in the azimuth direction by one element so that an ultrasonic beam is transmitted by using three elements $52d$ to $52f$ as transmit elements and an ultrasonic echo is received by using seven elements $52b$ to $52h$ as receive elements. Accordingly, respective pieces of element data are acquired.

That is, the element $52d$ is the central element (the element serving as the center) in the example illustrated in FIG. 4A, and the element $52e$ is the central element in the example illustrated in FIG. 4C.

Consideration is now given to an ideal situation in which, as illustrated in FIG. 4A and FIG. 4C, an ultrasonic beam 56 transmitted to a region under examination including a reflection point 54 converges at a focal point 58 and is narrowed down to a value equal to or less than the element spacing.

As in FIG. 4A, element data is acquired by transmitting the ultrasonic beam 56 from the elements $52c$ to $52e$, which are the transmit elements, with the element $52d$ directly above the reflection point 54 (on a straight line connecting the reflection point and the focal point) being the central element, and by receiving an ultrasonic echo at the elements $52a$ to $52g$, which are the receive elements, resulting in the focal point 58 of the ultrasonic beam 56 being located on a straight line connecting the element $52d$, which is the central element, and the reflection point 54. In this case, the ultrasonic beam 56 is transmitted to the reflection point 54 and an ultrasonic echo reflected from the reflection point 54 is generated accordingly.

The ultrasonic echo from the reflection point 54 travels through a receive path 60 that extends over a predetermined angle and is received by the elements 52a to 52g, which are the receive elements, and element data 62, as illustrated in FIG. 4B, is obtained by the elements 52a to 52g. Note that, in FIG. 4B, the vertical axis represents time and the horizontal axis represents positions (the positions of the respective elements) in the azimuth direction, which match those in FIG. 4A (the same applies to FIG. 4D).

In contrast, as illustrated in FIG. 4C, when the central element is shifted by one element, the element 52e, which is adjacent to the element 52d directly above the reflection point 54, becomes the central element.

The ultrasonic beam 56 is transmitted from the elements 52d to 52f, which are the transmit elements, with the element 52e being the central element, and an ultrasonic echo is received by the elements 52b to 52h, which are the receive elements. At this time, if the ultrasonic beam 56 is also ideal, the reflection point 54 is not located in the transmit direction of the ultrasonic beam 56, that is, on a straight line connecting the central element 52e and the focal point 58. Thus, the ultrasonic beam 56 is not transmitted to the reflection point 54.

Accordingly, an ultrasonic echo reflected from the reflection point 54 is not generated, and the elements 52b to 52h, which are the receive elements, do not receive any ultrasonic echo from the reflection point 54. Thus, as illustrated in FIG. 4D, the element data does not include reflected signals from the reflection point (the element data has a signal intensity of "0").

An actual ultrasonic beam, however, like an ultrasonic beam 64 illustrated in FIG. 5A and FIG. 5C, is diffused after converging at the focal point 58, and thus has a width larger than the element spacing.

Here, as in FIG. 5A, the ultrasonic beam 64 is transmitted in a manner similar to that in FIG. 4A by using the elements 52c to 52e as transmit elements with the element 52d directly above the reflection point 54 being the central element. In this case, even if the ultrasonic beam 64 is wide, the focal point 58 thereof is located on a straight line connecting the element 52d and the reflection point 54. Accordingly, the ultrasonic beam 64 is reflected from the reflection point 54 and an ultrasonic echo is generated.

As a result, in a manner similar to that in FIG. 4A, the ultrasonic echo from the reflection point 54 travels through a receive path 60 extending over a predetermined angle and is received by the elements 52a to 52g, which are the receive elements. In a similar manner, element data 66 (hereinafter also referred to as "true element data", for convenience) including a true signal, as illustrated in FIG. 5B, is obtained.

Then, as illustrated in FIG. 5C, the central element is shifted by one element, in a manner similar to that in FIG. 4C, so that the ultrasonic beam 64 is transmitted by using the elements 52d to 52f as transmit elements, with the adjacent element 52e being the central element, and an ultrasonic echo is received by using the elements 52b to 52h as receive elements. Also in this case, since the ultrasonic beam 64 is wide, the ultrasonic beam 64 is transmitted to (arrives at) the reflection point 54 if the reflection point 54 is not located in the transmit direction of the ultrasonic wave, that is, on a straight line connecting the element 52e, which is the central element, and the focal point 58.

Accordingly, an ultrasonic echo that would not be otherwise present, called a ghost reflected echo, emanates from the reflection point 54 in the transmit direction of the ultrasonic beam 64. As illustrated in FIG. 5C, the ghost reflected echo from the reflection point 54 travels through a receive path 60 extending over a predetermined angle and is received by the elements 52b to 52h, which are the receive elements. As a result, element data 68 (hereinafter referred to also as "ghost element data", for convenience) including a ghost signal, as illustrated in FIG. 5D, is obtained by the elements 52b to 52h.

The ghost element data 68 causes a reduction in the accuracy of an ultrasound image generated from element data.

The element data processing unit 22 is configured such that the delay time calculation unit 48 calculates a delay time for element data and the superimposition processing unit 49 superimposes two or more pieces of element data in accordance with the delay time and the absolute positions of the elements to generate processed element data that is accurate element data with a true signal enhanced and a ghost signal attenuated.

As described above, the delay time calculation unit 48 calculates a delay time for element data received by each of the elements of the receive elements (receive apertures).

Specifically, the propagation distance of the ultrasonic beam 64 illustrated in FIG. 5C is the sum of a transmit path along which the ultrasonic beam 64 from the element 52e, which is the central element, travels through the focal point 58 and reaches the reflection point 54 and a receive path along which the ghost reflected echo from the reflection point 54 reaches each of the elements 52b to 52h, which are the receive elements.

The propagation distance of the ultrasonic beam 64 illustrated in FIG. 5C is longer than the propagation distance of the ultrasonic beam 64 illustrated in FIG. 5A, that is, the sum of a transmit path along which the ultrasonic beam 64 from the central element 52d travels through the focal point 58 and reaches the reflection point 54 and a receive path along which the true ultrasonic echo from the reflection point 54 reaches the elements 52a to 52g, which are the receive elements.

For this reason, the ghost element data 68 as illustrated in FIG. 5D is delayed with respect to the true element data 66 as illustrated in FIG. 5B.

In the delay time calculation unit 48 of the element data processing unit 22, the time difference of the ghost element data with respect to the true element data, or the delay time, is calculated from the sound velocity and the geometric arrangement of the transmit elements, the focal point of the ultrasonic beam, the reflection point in the subject, and the receive elements.

Accordingly, the computation of the delay time requires information such as the shape of the probe 12 (such as the element spacing and linear or convex), the sound velocity, the position of the focal point, the transmit apertures, and the receive apertures. The delay time calculation unit 48 acquires these pieces of information, which are input by using the operation unit 32 or stored in the storage unit 34, and computes the delay time.

Note that the sound velocity may have a fixed value (for example, 1540 m/sec), or, if a sound velocity calculation unit is included, a sound velocity (ambient sound velocity) calculated by the sound velocity calculation unit may be used. Alternatively, an operator may be able to input a sound velocity.

The delay time can be calculated from the difference in the propagation time calculated from the sound velocity and the total length (propagation distance) of a transmit path along which an ultrasonic beam from transmit elements travels through a focal point and reaches a reflection point and a receive path along which a true reflected ultrasonic echo or a ghost reflected signal from the reflection point reaches receive elements, the total length (propagation distance) being calculated from the geometric arrangement of the transmit elements, the focal point of the ultrasonic beam, the reflection point in the subject, and the receive elements, for example.

Figure 6A:
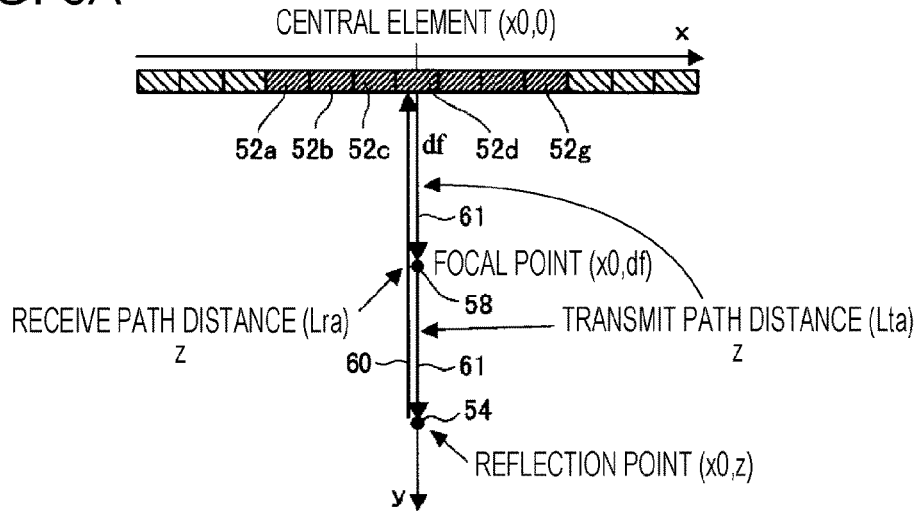
FIG. 6A and FIG. 6B are conceptual diagrams for describing a path of a sound wave in a case where the transmission and reception of ultrasonic waves are performed by different central elements with respect to the same reflection point.
Figure 6B:
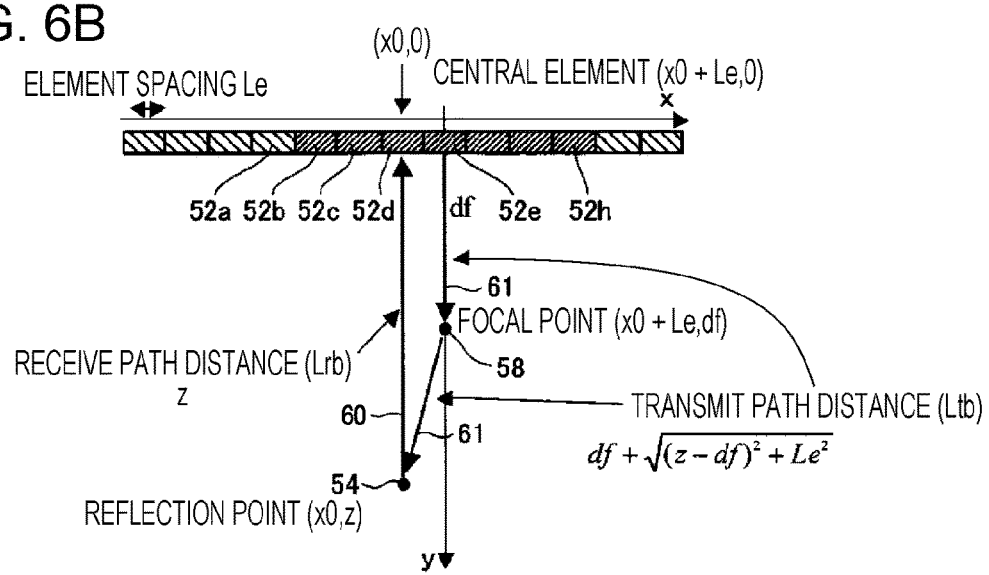

In the present invention, the length of the transmit path and receive path of an ultrasonic beam in the case of a true ultrasonic echo and a ghost reflected echo can be determined in a way illustrated in FIG. 6A and FIG. 6B, for example. Note that, in FIG. 6A and FIG. 6B, the x direction represents the azimuth direction and the y direction represents the depth direction.

In addition, FIG. 6A depicts the transmission and reception of ultrasonic waves which is performed in a manner similar to that in FIG. 5A, and FIG. 6B depicts the transmission and reception of ultrasonic waves which is performed in a manner similar to that in FIG. 5C.

In the case of a true ultrasonic echo, as illustrated in FIG. 6A (FIG. 5A), the element 52*d*, which is the central element, the focal point 58, and the reflection point 54 are positioned on a straight line (the positions thereof in the azimuth direction coincide with one another). That is, the focal point 58 and the reflection point 54 are located directly below the central element 52*d*.

Thus, assuming that the position of the element 52*d*, which is the central element, is given by the coordinates (x0, 0) on the two-dimensional x-y coordinate system, the x coordinates of both the focal point 58 and the reflection point 54 are also given by "x0". In the following, the position of the focal point 58 in this transmission is given by the coordinates (x0, df), the position of the reflection point 54 is given by the coordinates (x0, z), and the spacing of each element is denoted by Le.

In this case, the length (transmit path distance) Lta of a transmit path 61 of an ultrasonic beam from the element 52*d*, which is the central element, that travels through the focal point 58 and reaches the reflection point 54, and the length (receive path distance) Lra of a receive path 60 of a true reflected ultrasonic echo from the reflection point 54 that reaches the element 52*d* can be calculated by Lta=Lra=z.

In the case of a true ultrasonic echo, therefore, an ultrasonic echo propagation distance Lua is given by Lua=Lta+Lra=2z.

Then, as illustrated in FIG. 6B, the transmit elements and the receive elements are shifted by one element in the x direction (azimuth direction) (shifted rightward in the diagram) so that transmission and reception are performed with the element 52*e* being the central element. In this case, as illustrated in FIG. 5C, a ghost reflected echo is reflected by the reflection point 54.

The reflection point 54 is located directly below the element 52*d* (at the same position in the azimuth direction). Therefore, as illustrated in FIG. 6B, in this transmission and reception, the positions of the element 52*e*, which is the central element, and the reflection point 54 in the x direction are displaced from each other by one element, that is, by Le, in the x direction.

Since the coordinates of the element 52*d* whose position in the x direction coincides with that of the reflection point 54 are (x0, 0), the coordinates of the element 52*e*, which is the central element, are (x0+Le, 0) and the coordinates of the focal point 58 in this transmission are (x0+Le, df). Note that the coordinates of the reflection point 54 are (x0, z), as described above.

Accordingly, the length (transmit path distance) Ltb of a transmit path 61 of an ultrasonic beam from the element 52*e*, which is the central element, that travels through the focal point 58 and reaches the reflection point 54 can be calculated by Ltb=df+$\sqrt{\{(z-df)^2+Le^2\}}$. On the other hand, the length (receive path distance) Lrb of a receive path 60 of a ghost reflected signal from the reflection point 54 that reaches the element 52*d* directly thereabove (at the same position in the x direction=the azimuth direction) can be calculated by Lrb=z.

Thus, an ultrasonic wave propagation distance Lub in the case of a ghost reflected echo is given by Lub=Ltb+Lrb=df+$\sqrt{\{(z-df)^2+Le^2\}}$+Z.

In this manner, a value obtained by dividing the ultrasonic wave propagation distance Lua determined by using the geometric arrangement illustrated in FIG. 6A, which is the sum of the distance Lta of the transmit path 61 and the distance Lra of the receive path 60, by the sound velocity corresponds to the true ultrasonic echo propagation time. Further, a value obtained by dividing the ultrasonic wave propagation distance Lub determined by using the geometric arrangement illustrated in FIG. 6B, which is the sum of the distance Ltb of the transmit path 61 and the distance Lrb of the receive path 60, by the sound velocity corresponds to the ghost reflected echo propagation time.

The delay time is determined from the difference between the true ultrasonic echo propagation time obtained when the x coordinates of the reflection point 54 and the central element coincide with each other and the ghost reflected echo propagation time obtained when the x coordinates of the reflection point 54 and the central element are displaced from each other by the spacing of one element.

Note that the geometric models in FIG. 6A and FIG. 6B are models in which the transmit path 61 passes through the focal point 58; however, the present invention is not limited thereto. For example, a path which directly reaches the reflection point 54 without passing through the focal point 58 may be used.

In addition, the geometric models in FIG. 6A and FIG. 6B are based on, but are not limited to, the case of a linear probe. Any other probe may also be used to perform similar geometric computation in accordance with the shape of the probe.

For example, in the case of a convex probe, a geometric model can be set from the radius of the probe and the angle defined by the element spacing and computation can be performed in a similar way.

Furthermore, in the case of steer transmission, a geometric model that takes into account information such as transmit angle can be used, and the delay times of true element data and neighboring ghost element data can be calculated based on the positional relationship between the transmit elements and the reflection point.

Moreover, instead of a method of calculating a delay time by using a geometric model, the following method may be used. A delay time is determined in advance for each measurement condition from measurement results obtained by measuring a high-brightness reflection point in accordance with the measurement conditions of the apparatus, and is stored in the apparatus to allow the delay time for the same measurement condition to be read.

Alternatively, if a delay time is changed by the setting changing unit 23, the delay time to be used may be set on the basis of delay time information supplied from the setting changing unit 23.

Figure 6C:
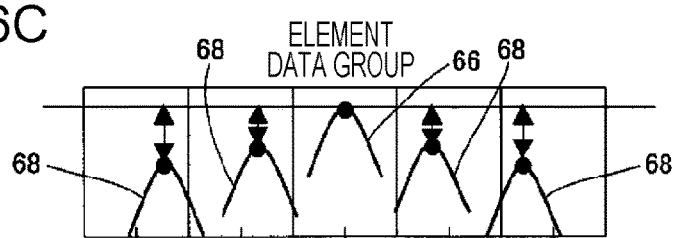
FIG. 6C is a conceptual diagram for describing pieces of element data obtained by a plurality of elements.

FIG. 6C illustrates the true element data 66 and the ghost element data 68.

In FIG. 6C, the true element data 66, that is, element data obtained by transmission and reception with the central element and the reflection point 54 whose positions in the x direction coincide (in the illustrated example, element data obtained when the element 52*d* is the central element), is illustrated in the center in the azimuth direction. Further, depicted on either side of the center is ghost element data, that is, element data obtained by transmission and reception with the central element and the reflection point 54 whose positions in the x direction do not coincide (in the illustrated example, element data obtained when the element 52*c*, the element 52*e*, or the like is the central element).

Figure 6D:
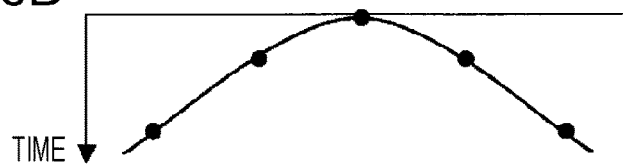
FIG. 6D is a conceptual diagram for describing delay times of the pieces of element data illustrated in FIG. 6C.

Further, FIG. 6D illustrates an example of the delay times of the ghost element data 68 with respect to the true element data 66, which are obtained from the geometric computation described above. The illustration shows that the pieces of element data 68 of the ghost signals are symmetrically delayed in time with respect to the true element data 66 in the x direction, that is, in the azimuth direction.

Note that the delay times calculated by the delay time calculation unit 48 of the element data processing unit 22 in the way described above can also be used for delay correction performed in the phasing addition unit 38.

Though described below in detail, in the invention, element data obtained by transmission of an ultrasound beam, for which the central element is different and at least a part of the ultrasound beam overlaps, is superimposed on element data obtained by transmission with a certain element of interest as a central element (transmission and reception of an element of interest) according to the reception time of the ultrasonic echo and the position of the element to generate processed element data (second element data) of the element of interest (to reconstruct element data of the element of interest).

In FIG. 6A, the reflection point 54 represents the position of a certain sampling point (the output position of the element data) positioned directly below the element of interest (at the same position in the azimuth direction/on a straight line connecting the element of interest and the focal point). In the present invention, a transmit/receive path to/from a sampling point in transmission and reception for the element of interest is regarded as a transmit/receive path of true element data and a transmit/receive path to/from the same sampling point in the transmission and reception of ultrasonic waves for which a different central element is used (transmission and reception from a neighboring element) is regarded as a transmit/receive path of ghost element data. A delay time is calculated by using the difference between both transmit paths, and is used for superimposition of element data in such a manner that their times are aligned. In other words, a delay time is calculated, assuming that element data obtained by transmission and reception for the element of interest is true element data and element data obtained by transmission and reception for a different central element is ghost element data, and the pieces of element data are superimposed.

In the present invention, a similar concept is used to calculate delay times for all the sampling points (the output positions of all the pieces of element data) for superimposition of element data, and processed element data of each element is generated.

Here, actually, the length of the receive path (the receive path distance Lrb) does not change even if the position of the sampling point (reflection point) is shifted in the azimuth direction (x direction). It is therefore sufficient to calculate a delay time for each element of interest with respect to element data obtained by transmission and reception for a different central element at each sampling point in the depth direction (y direction).

In this superimposition processing, furthermore, it is not necessary to know which element data is true element data. That is, as described in detail below using parts (a) to (h) of FIG. 7, in this superimposition processing, a signal included in element data is automatically enhanced and remains if the signal is a true signal, and is canceled if the signal is a ghost signal. That is, if a reflection point is located on the line of the element of interest, a signal from the reflection point is enhanced since the processes based on the delay times match, whereas a signal from a reflection point on a line other than the line of the element of interest is canceled since the processes based on the delay times do not match.

Then, the superimposition processing unit 49 of the element data processing unit 22 of the present invention performs superimposition processing on the element data by using the delay time calculated by the delay time calculation unit 48 in the way described above.

Note that the superimposition processing performed in the superimposition processing unit 49 requires information on the number of pieces of element data to be superimposed and the superimposition processing method. These pieces of information may be input by using the operation unit 32 in advance or stored in the storage unit 34 in advance.

Parts (a) to (h) of FIG. 7 illustrate an example of the superimposition processing performed in the superimposition processing unit 49. Note that the example illustrated in parts (a) to (h) of FIG. 7 depicts the case where the number of pieces of element data is five and the number of pieces of element data to be superimposed is three.

In part (a) of FIG. 7, five pieces of element data obtained by five transmissions and receptions of ultrasonic waves are displayed side by side. Part (a) of FIG. 7 further depicts transmission of an ultrasonic beam and reception of ultrasonic echoes for each piece of element data. The horizontal axis of the plot of each piece of element data represents receive elements that are depicted centered on the central element in the transmission and reception of ultrasonic beams for each piece of element data. The vertical axis represents reception time. In this example, transmission and reception of ultrasonic waves are performed five times with the central element shifted one by one, for example, the elements 52*b* to 52*f*.

Part (a) of FIG. 7 illustrates a state in which a single reflection point is located only directly below the central element in the element data depicted at the center. That is, in the element data in the middle of the five pieces of element data, a true ultrasonic echo from the reflection point is received in the transmission and reception of the ultrasonic wave. That is, the element data in the middle is true element data.

For the two pieces of element data on either side other than the element data in the middle, the reflection point is not located directly below the central elements in the transmission and reception of ultrasonic waves. However, due to the spread of the transmitted ultrasonic beams, element data of reflected echoes produced by the ultrasonic beams impinging on the reflection point located directly below the transmit element for the element data in the middle, that is, ghost element data, appears.

The farther the ghost element data from the true element data, the longer the ultrasonic wave propagation time to the reflection point. Thus, the reception time of the ghost element data is later than that of the true element data. In addition, the receive element that is first to receive the ultrasonic echo from the reflection point is an element located immediately above the reflection point (an element whose position in the azimuth direction coincides with that of the reflection point).

Here, the horizontal axis of the plot of each piece of element data in part (a) of FIG. 7 is centered on the central element in the transmission of an ultrasonic beam. In the example illustrated in part (a) of FIG. 7, therefore, since transmission is performed with the central element shifted by one element for each piece of element data, the absolute positions of the respective elements in the azimuth direction are shifted by one element for each piece of element data. Specifically, for the element data in the middle, the receive element that is first to receive a reflected signal from the reflection point is the central element, whereas, for the element data on either side of the element data in the middle, this receive element is shifted by one element with respect to that for the element data in the middle in such a manner that, for the element data on the right side, this receive element is shifted to the left by one element and, for the element data on the left side, this receive element is shifted to the right by one element. For the element data at either end, furthermore, this receive element is shifted by two elements with respect to that for the element data in the middle in such a manner that, for the element data at the right end, this receive element is shifted to the left by two elements and, for the element data at the left end, this receive element is shifted to the right by two elements. In this manner, for the ghost signals, in addition to the reception times being delayed with respect to that of the true signal, the receive elements are also shifted in the direction thereof.

Part (b) of FIG. 7 illustrates an example of the delay times regarding the reception times with respect to the reception time of the element data in the middle of the five pieces of element data illustrated in part (a) of FIG. 7.

By using the delay times illustrated in part (b) of FIG. 7, the superimposition processing unit 49 performs delay-time correction on a number of pieces of element data to be superimposed, e.g., three pieces of element data in the illustrated example, centered on the element data of an element of interest, where the element of interest is the central element for the element data in the middle. In addition, the superimposition processing unit 49 superimposes the pieces of unprocessed element data for the three pieces of element data with each piece of element data shifted in accordance with the difference between the position of the corresponding element and the position of the element of interest (the difference in position between the central elements), e.g., with the element data on either side shifted by one element in the azimuth direction in the illustrated example, that is, with their phases aligned, to determine a piece of superimposition-processed element data for the element of interest.

That is, this example involves superimposing, on element data obtained by transmission and reception of ultrasonic waves with the element of interest being the central element (hereinafter also referred to as the element data for the element of interest), element data obtained by transmission and reception of ultrasonic waves with an element adjacent to the element of interest being the central element (hereinafter also referred to as the element data for the adjacent element) to generate processed element data of the element data for the element of interest.

Part (c) of FIG. 7 illustrates the superimposition-processed element data for the element of interest obtained in the way described above.

As described above, the element data for the element of interest illustrated in part (a) of FIG. 7 is true element data for which the reflection point is located directly below the central element (i.e., the element of interest). In addition, element data obtained by transmission and reception for which an element adjacent to the element of interest is the central element is also data of an ultrasonic echo reflected from the reflection point to which the ultrasonic beam is incident.

Accordingly, the element data for the adjacent element on either side of the element data for the element of interest is subjected to delay-time correction and to a shift in the azimuth direction to perform phase alignment. In consequence, as illustrated in part (c) of FIG. 7, the pieces of element data for the adjacent elements and the element data for the element of interest are superimposed at a high-brightness position since their phases are aligned. Therefore, for example, these pieces of element data are summed, resulting in the element data value being a large value (high-brightness value). For example, the pieces of element data are averaged to obtain an average value which is also an enhanced value (high-brightness value).

In contrast, part (d) of FIG. 7 illustrates an example of the case in which, while the same element data as that in part (a) of FIG. 7 is used, the element of interest is the central element for the element data that is left-adjacent to the element data in the middle. That is, this example is an example of the case in which, in the transmission and reception of ultrasonic waves with the central element being an element directly below which the reflection point is not located, the central element is the element of interest. Thus, element data for which this element is the central element is ghost element data.

Part (e) of FIG. 7 corresponds to part (b) of FIG. 7, and illustrates an example of the delay times regarding the reception times of the five pieces of element data illustrated in part (d) of FIG. 7 with respect to the reception time of the element data for the element of interest. That is, since parts (a) and (d) of FIG. 7 illustrate the same element data, the illustrated delay times are also the same as the delay times regarding the reception times of the five pieces of element data illustrated in part (a) of FIG. 7 with respect to the reception time of the element data in the middle.

The superimposition processing unit 49 performs delay-time correction on a number of pieces of element data to be superimposed, e.g., three pieces of element data in the illustrated example, centered on the element data for the element of interest by using the delay times illustrated in part (e) of FIG. 7 (i.e., the same as those in part (b) of FIG. 7). In addition, the superimposition processing unit 49 superimposes the pieces of unprocessed element data for the three pieces of element data with each piece of element data shifted in accordance with the difference between the position of the corresponding element and the position of the element of interest (the difference in position between the central elements), e.g., with the element data on either side shifted by one element in the azimuth direction in the illustrated example, to determine a piece of superimposition-processed element data for the element of interest.

Part (f) of FIG. 7 illustrates the superimposition-processed element data for the element of interest obtained in the way described above.

The element data for the element of interest illustrated in part (d) of FIG. 7 is ghost element data. Thus, even if unprocessed element data for the adjacent element on either side of the element data for the element of interest is subjected to delay-time correction and to a shift in the azimuth direction to perform phase alignment, as illustrated in part (f) of FIG. 7, the pieces of element data for the adjacent elements and the element data for the element of interest are not superimposed since their phases are not aligned. Therefore, for example, if these three pieces of element data are summed, the resulting sum value is not large because the phases of the pieces of element data are not aligned and phase-inverted signals would cancel each other out, for example. For example, the pieces of element data are averaged to obtain an average value which is a small value.

Part (g) of FIG. 7 illustrates the states of superimposed three pieces of adjacent element data for the five pieces of element data in the illustrated example as a result of also subjecting each of the other pieces of element data to similar delay-time correction and to a shift in the azimuth direction as element data for the element of interest. Part (h) of FIG. 7 illustrates the result of subjecting these pieces of element data to superimposition processing, namely, summing processing or averaging processing, for example.

As illustrated in part (h) of FIG. 7, when a central element directly below which the reflection point is located, as illustrated in part (a) of FIG. 7, is used as an element of interest, element data of a true signal is determined as superimposition-processed element data having high-brightness values. In two pieces of element data on either side, or four pieces of element data in total, on the other hand, the sum or average of pieces of element data whose phases are not aligned with each other is taken for ghost element data. This allows the pieces of element data to cancel each other out, resulting in the ghost superimposition-processed element data having values that are smaller than those of the superimposition-processed element data having high-brightness values, which is the element data of the true signal. The influence of the ghost element data on the true element data can be reduced or can be small to be negligible.

That is, superimposing, on element data obtained by transmission of an ultrasonic beam with an element of interest being the central element (element data for the element of interest), where the element of interest is a certain element, one or more pieces of element data obtained by transmission and reception of ultrasonic waves for which a different central element is used and for which a transmission region of the ultrasound beam overlaps in such a manner that the times and the positions in the azimuth direction are aligned to generate processed element data corresponding to the element data for the element of interest (in other words, to reconstruct (correct) the element data for the element of interest by using element data obtained by transmission and reception of an ultrasonic beam at least part of which overlaps that for the element of interest and for which a different central element is used) can increase the brightness of true element data and can reduce ghost element data.

Accordingly, processed element data is subjected to phasing addition or detection processing to generate reception data to generate an ultrasound image. This enables an ultrasound image to be generated from element data which is free of influence of ghosting and for which it is equivalent to saying that every point on a sound ray is brought into focus. Thus, a high-brightness, high-quality ultrasound image with good sharpness can be generated.

Note that, in the following description, the generation of processed element data is also referred to as multi-line processing.

Furthermore, the processed element data is a piece of processed data in the present invention.

In the present invention, the term central element refers to the element at the center in the azimuth direction when the number of apertures for transmission (the number of elements that transmit ultrasonic waves) is an odd number.

On the other hand, when the number of apertures is an even number, any one of the elements located in the center in the azimuth direction is used as the central element or an element assumed to be located in the middle in the azimuth direction is used as the central element. That is, when the number of apertures is an even number, computation may be performed assuming that the focal point is located on a line in the middle of the apertures.

Note that the superimposition processing method in the superimposition processing unit 49 may involve taking an average value or a median value, as well as simply performing summation, or performing summation after multiplication with a coefficient. Note that while taking an average value or a median value may be considered to be equivalent to applying an averaging filter or a median filter in the element data level, an inverse filter or any other filter used in typical image processing may be applied instead of an averaging filter or a median filter.

The above disclosure is not intended to be limiting. Alternatively, the superimposition processing may be changed on the basis of the respective feature values of the pieces of element data to be superimposed. For instance, the pieces of element data to be superimposed may be compared, and a maximum value may be taken when they are similar, an average value may be taken when they are not similar, or an intermediate value may be taken when there is a biased distribution.

In addition, the number of pieces of element data to be superimposed on the element data for the element of interest is not limited to two, as in illustrated example, and may be one or more than two. That is, the number of pieces of element data to be superimposed on the element data for the element of interest may be set, as appropriate, in accordance with the required processing speed (such as the frame rate), image quality, and so on. Basically, the larger the number of pieces of element data to be superimposed, the more the image quality improved.

Here, it is desirable that the number of pieces of element data to be superimposed on the element data for the element of interest be determined in accordance with the degree of the spread of the beam width of the ultrasonic beam. Accordingly, when the beam width varies depending on the depth, the number of pieces of element data to be superimposed may also be changed depending on the depth.

In addition, since the beam width depends on the number of transmit apertures, the number of pieces of element data to be superimposed may be changed in accordance with the number of transmit apertures. Alternatively, the number of pieces of element data to be superimposed may be changed on the basis of a feature value such as a luminance value of an image, or an optimum number of pieces of element data to be superimposed may be selected from images created by changing the number of pieces of element data to be superimposed in accordance with a plurality of patterns.

In addition, the processed element data generated through superimposition does not need to correspond to any one of the pieces of unprocessed element data to be used for superimposition. That is, generated processed element data may be data corresponding to a position (line) different from that for the unprocessed element data.

For example, processed element data corresponding to a line at the intermediate position of the lines corresponding to the respective pieces of unprocessed element data may be generated.

In addition, the number of lines for which processed element data is generated may be equal to or larger or smaller than the number of lines for which unprocessed element data has been acquired (the number of lines on which transmission and reception of ultrasonic waves have been performed).

Specifically, for example, processed reception data corresponding to lines for which unprocessed element data has been acquired and a line at the intermediate position of the lines may be generated to generate processed reception data corresponding to lines, the number of which is twice as large as the number of lines on which transmission and reception of ultrasonic waves have been performed.

Note that, in the foregoing multi-line processing, pieces of element data obtained by transmission of a plurality of ultrasonic beams for which the central elements are different and whose transmit directions are parallel (whose angles are identical) are superimposed to generate processed element data of element data for an element of interest; however, the present invention is not limited thereto.

For example, pieces of element data obtained by transmission of a plurality of ultrasonic beams for which the central elements are identical and whose transmit directions (angles) are different may be superimposed to generate processed element data. In this case, which ultrasonic beam is transmitted to obtain processed element data of element data to be generated (that is, in which direction of sound ray to generate processed element data) may be set by default in accordance with the part to be diagnosed, the type of the probe, or the like, or may be selected by an operator.

Alternatively, element data obtained by transmission of parallel ultrasonic beams for which the central elements are different and element data obtained by transmission of ultrasonic beams for which the central elements are identical and whose transmit directions are different may be both used to generate processed element data.

As described above, the element data processing unit 22 delivers the generated processed element data to the image generation unit 24 (the phasing addition unit 38).

In the image generation unit 24 to which the processed element data is supplied, as described above, the phasing addition unit 38 executes phasing addition on the processed element data to perform a receive-focusing process and generates reception data, and the detection processing unit 40 performs attenuation correction and envelope detection processing on the reception data to generate B-mode image data.

In the image generation unit 24, furthermore, the DSC 42 raster-converts the B-mode image data into image data that supports a normal television signal scanning system, and the image processing unit 44 performs predetermined processing such as gradation processing.

The image processing unit 44 stores the generated B-mode image data in the image memory 46, and/or delivers it to the display control unit 26 to display a B-mode image of the subject on the display unit 28.

Here, as described above, if a measurement condition is changed, the setting changing unit 23 changes the setting of at least one of the transmitting unit 14, the receiving unit 16, the element data processing unit 22, the image generation unit 24, and the display control unit 26 on the basis of the setting information held in the setting information holding unit 21.

An example of the method of changing setting by using the setting changing unit 23 will be described in detail using FIG. 8 and FIG. 9A and FIG. 9B.

FIG. 8 is a conceptual diagram for describing ranges of sum lines (the number of superimpositions) before and after the change of the focal position as a measurement condition.

Note that FIG. 8 illustrates an imaging area, in which the horizontal direction corresponds to the arrangement direction of elements and the vertical direction corresponds to the depth direction.

First, before the change of the focal position, when multi-line processing is performed on a line of interest indicated by using the one-dot chain line in the diagram, the number of superimpositions for multi-line processing is assumed to be equal to the number of lines within a range represented by the broken line. The range of sum lines indicated by using the broken line in the diagram is set so as to be spread in both directions in the depth direction from the focal position so as to correspond to the width of the spread of the ultrasonic beam to be transmitted. That is, the number of superimpositions for multi-line processing is set so that the number of superimpositions is changed in accordance with the depth of the sampling point.

The setting information holding unit 21 acquires information on the number of superimpositions at predetermined timing and holds the information.

Then, if the focal position is changed as a measurement condition, the setting changing unit 23 acquires from the setting information holding unit 21 information on the number of superimpositions before the change of the measurement condition. The setting changing unit 23 sets, from the acquired information on the number of superimpositions and information on the changed focal position, the number of superimpositions for multi-line processing after the change of the measurement condition as the number of lines within the range indicated using the solid line in the diagram.

Specifically, the range indicated using the solid line is set so as to be spread in both directions in the depth direction from the focal position and so that the total number of sum lines for generating the processed element data for one line is equal to the total number of sum lines before the change of the measurement condition. That is, the number of superimpositions for multi-line processing after the change of the measurement condition is set so that the total numbers of sum lines for generating an image of one frame before and after the change of the measurement condition are equal.

This allows the numbers of times computation processing is performed and the computational loads before and after the change of the measurement condition to be the same, and allows the frame rates to be equal.

This configuration is an example of a configuration for changing setting of a data processing unit on the basis of setting information held in a setting information holding unit.

Here, the setting information holding unit 21 may hold, in addition to the information on the number of superimpositions before the change of the measurement condition, STC gain information for the image generation unit 24 (the detection processing unit 40). If a measurement condition is changed, the setting changing unit 23 may change the value of the STC gain in addition to the number of superimpositions.

As a result of multi-line processing, ghost signals are removed. This allows the luminance value of the image data to decrease as the number of superimpositions for multi-line processing increases. That is, in the illustrated example, the number of superimpositions after the change of the measurement condition is smaller than that before the change of the measurement condition in the upper portion in the drawing. Thus, the luminance value of the image to be generated is larger. In the middle to the bottom portion in the drawing, in contrast, the number of superimpositions after the change of the measurement condition is larger than that before the change of the measurement condition. Thus, the luminance value of the image to be generated is smaller.

Accordingly, the setting changing unit 23 sets the number of superimpositions for multi-line processing after the change of the measurement condition, and sets the STC gain in accordance with the set number of superimpositions.

This allows images generated in a case where the same subject is examined to have an equal luminance before and after the change of the measurement condition, and allows the images to be displayed without causing any uncomfortable feeling.

Note that the setting changing unit 23 may set the STC gain on the basis of a table in which relationships between the numbers of superimpositions and STC gain values are set in advance, or may set the STC gain on the basis of the number of superimpositions before the change of the measurement condition, the STC gain value, and the number of superimpositions after the change.

This configuration is an example of a configuration for changing setting of an image generation unit on the basis of setting information on a data processing unit which is held in a setting information holding unit.

In the example illustrated in FIG. 8, furthermore, the setting changing unit 23 is configured to set the STC gain so that images have an equal luminance before and after the change of the measurement condition. Alternatively, a configuration may be used in which the gain of the entire screen is set.

Next, a method for changing the number of superimpositions when the ultrasonic probe 12 is changed will be described using FIG. 9A and FIG. 9B.

FIG. 9A illustrates an imaging area before the change of the ultrasonic probe 12, in which the horizontal direction corresponds to the arrangement direction of elements and the vertical direction corresponds to the depth direction. Further, FIG. 9B illustrates an imaging area after the change of the ultrasonic probe 12, in which the circumferential direction corresponds to the arrangement direction of the elements and the radial direction corresponds to the depth direction.

That is, the illustrated example shows an example in the case where the ultrasonic probe 12 is changed from a linear probe (FIG. 9A) to a convex probe (FIG. 9B).

First, before the change of the ultrasonic probe 12, when multi-line processing is performed on a line of interest indicated by using the one-dot chain line in FIG. 9A, the number of superimpositions for multi-line processing is set to increase in both directions in the depth direction from the focal position in accordance with the width of the spread of the ultrasonic beam, as indicated by using the broken line.

The setting information holding unit 21 acquires information on the number of superimpositions at predetermined timing and holds the information.

Then, when the ultrasonic probe 12 is changed as a measurement condition, the setting changing unit 23 acquires from the setting information holding unit 21 information on the number of superimpositions before the change of the measurement condition, and sets, from the acquired information on the number of superimpositions and information on the changed ultrasonic probe, the number of superimpositions for multi-line processing after the change of the measurement condition as the number of lines within the range indicated using the solid line in the diagram.

Specifically, when an ultrasonic probe is changed, the sampling rate (the number of sampling points on a single line), the number of measured lines (the number of lines necessary to create a single image), and so on vary. Accordingly, the number of superimpositions after the change of the measurement condition is set from the sampling rates before and after the change of the measurement condition, the number of measured lines, and information on the number of superimpositions before the change of the measurement condition so that the total numbers of sum lines for generating an image of one frame are equal.

This allows the numbers of times computation processing is performed and the computational loads before and after the change of the measurement condition to be the same, and allows the frame rates to be identical.

This configuration is an example of a configuration for changing setting of a data processing unit on the basis of setting information held in a setting information holding unit.

In addition, similarly to the example illustrated in FIG. 8, the setting information holding unit 21 may hold, in addition to the information on the number of superimpositions before the change of the measurement condition, STC gain information for the image generation unit 24 (the detection processing unit 40). If a measurement condition is changed, the setting changing unit 23 may change the value of the STC gain in addition to the number of superimpositions.

This allows, also if an ultrasonic probe is changed, images generated in a case where the same subject is examined to have an equal luminance before and after the change, and allows the images to be displayed without causing any uncomfortable feeling.

This configuration is an example of a configuration for changing setting of an image generation unit on the basis of setting information on a data processing unit which is held in a setting information holding unit.

The method of changing setting by using the setting changing unit 23 is not limited to the examples illustrated in FIG. 8, FIG. 9A and FIG. 9B.

For example, a configuration may be used in which, when a probe is changed as a measurement condition, the setting information holding unit 21 holds the number of superimpositions for superimposition and the weighting factor (apodization factor) before the change of the probe, and the setting changing unit 23 sets the number of superimpositions and the apodization factor so that the total number of sum lines per frame and the image luminance after the change of the probe are equal to those before the change of the measurement condition.

Alternatively, another configuration may be used in which the setting information holding unit 21 holds the number of superimpositions for superimposition and the sampling frequency before the change of the probe and the setting changing unit 23 sets the number of superimpositions and the sampling frequency so that the total number of sum lines per frame and the image luminance after the change of the probe are equal to those before the change of the measurement condition.

In addition, a configuration may be used in which, when the frame rate is changed as a measurement condition, the setting information holding unit 21 holds the number of superimpositions before the change of the probe and, after the change of the frame rate, the setting changing unit 23 sets the number of superimpositions so as to achieve the total number of sum lines which can maintain the frame rate.

Furthermore, similarly to the example described above, a configuration may be used in which the setting information holding unit 21 also holds the gain (STC gain) and, after the change of the measurement condition, the setting changing unit 23 sets the gain (STC gain) so that images have an equal luminance.

Another configuration may be used in which, when the transmit aperture is changed as a measurement condition, similarly to the example illustrated in FIG. 8 in which the focal position is changed as a measurement condition, the setting changing unit 23 sets the number of superimpositions so that the range of sum lines in the superimposition processing corresponds to the width of the spread of the ultrasonic beam and, in addition, the total number of sum lines is equal to that before the change of the measurement condition.

Furthermore, similarly to the example described above, a configuration may be used in which the setting information holding unit 21 also holds the gain (STC gain) and, after the change of the measurement condition, the setting changing unit 23 sets the gain (STC gain) so that images have an equal luminance.

Here, the effect of multi-line processing is more suitably exerted if the difference in delay time between the pieces of element data to be superimposed in the superimposition processing is approximately one-half the period of the transmit frequency and/or the receive frequency. That is, the line (element data) suitable for superimposition varies in accordance with the transmit frequency and/or the receive frequency.

Thus, a configuration may be used in which, when the transmit frequency and/or the receive frequency is changed as a measurement condition, the setting information holding unit 21 holds the number of superimpositions and the gain (STC gain) before the change of the probe and the setting changing unit 23 sets the number of superimpositions and the gain (STC gain) so that the lines (element data) used for superimposition are changed in accordance with the frequency and, in addition, the total numbers of sum lines are equal and the images have an equal luminance before and after the change of the measurement condition.

Another configuration may be used in which, when the measurement mode is changed as a measurement condition, the setting information holding unit 21 holds the number of superimpositions and the gain (STC gain) before the change of the probe and the setting changing unit 23 sets the number of superimpositions and the gain (STC gain) so that the total number of sum lines per frame and the image luminance after the change of the probe are equal to those before the change of the measurement condition.

A signal processing method (signal processing method of the present invention) in the ultrasonic diagnostic apparatus 10 will be described in detail hereinafter with reference to a flowchart illustrated in FIG. 10A and FIG. 10B.

Note that a program of the present invention is a program for causing a computer included in the ultrasonic diagnostic apparatus 10 to execute the following signal processing method.

As illustrated in FIG. 10A, in the ultrasonic diagnostic apparatus 10, first, in accordance with instructions given from the control unit 30, in order to acquire element data, the transmitting unit 14 drives corresponding ultrasonic transducers (elements) of the probe 12 (the vibrator array 36) (with a predetermined number of apertures and at a predetermined aperture position) at a set transmit frequency to transmit an ultrasonic beam to the subject, an ultrasonic echo reflected by the subject is received by ultrasonic transducers (elements), and analog reception signals are output to the receiving unit 16.

The receiving unit 16 performs predetermined processing such as amplification on the analog reception signals, and supplies the resulting signals to the A/D conversion unit 18.

The A/D conversion unit 18 performs A/D conversion on the analog reception signals supplied from the receiving unit 16 to produce element data that is digital reception signals.

The element data is stored in the element data storage unit 20.

The element data processing unit 22 sequentially reads the element data stored in the element data storage unit 20 and performs multi-line processing to generate processed element data.

Specifically, as illustrated in parts (a) to (h) of FIG. 7 described above, the element data processing unit 22 calculates, for example, for an element of interest and elements adjacent to the element of interest, the delay times of the element data for the adjacent elements with respect to the element data for the element of interest, subjects the element data for the adjacent elements to delay-time correction and to a shift in the azimuth direction, and superimposes, on the element data for the element of interest, the element data for the adjacent elements on both sides thereof to generate processed element data for the element of interest.

The element data processing unit 22 superimposes element data for each of the pieces of element data corresponding to a predetermined plurality of lines to generate a plurality of pieces of processed element data. The element data processing unit 22 supplies the generated pieces of processed element data to the image generation unit 24. The image generation unit 24 generates an ultrasound image (B-mode image data) by using the pieces of processed element data. The generated ultrasound image is supplied to the display control unit 26 and is displayed on the display unit 28.

Here, the setting information holding unit 21 acquires and holds at least one of setting information on the transmitting unit 14 and the receiving unit 16 for the transmission and reception of an ultrasonic wave, setting information on the element data processing unit 22 for element data processing (multi-line processing), setting information on the image generation unit 24 for image generation, and setting information on the display control unit 26 for image display.

Then, as illustrated in FIG. 10B, when a measurement condition is changed, the setting changing unit 23 reads the setting information held in the setting information holding unit 21, and changes, on the basis of the setting information, at least one of the setting of the transmitting unit 14 and the receiving unit 16 for the transmission and reception of an ultrasonic wave, the setting of the element data processing unit 22 for element data processing (multi-line processing), the setting of the image generation unit 24 for image generation, and the setting of the display control unit 26 for image display.

When the setting is changed by the setting changing unit 23, the part whose setting has been changed performs processing based on the new setting, and an ultrasound image is generated and displayed on the display unit 28.

In this manner, when a measurement condition is changed, the setting after the change of the measurement condition is changed on the basis of setting information before the change of the measurement condition. This can prevent a large change in image lightness or frame rate.

Note that while the first embodiment is configured such that the element data processing unit 22 performs multi-line processing by using element data, the present invention is not limited thereto and a configuration may be used in which first reception data obtained by performing phasing addition on first element data is subjected to multi-line processing.

FIG. 11 conceptually illustrates in block diagram form an example of an ultrasonic diagnostic apparatus 110 according to a second embodiment of the present invention.

Note that the ultrasonic diagnostic apparatus 110 illustrated in FIG. 11 has the same configuration as that of the ultrasonic diagnostic apparatus 10 illustrated in FIG. 1, except that the ultrasonic diagnostic apparatus 110 includes a data processing unit 114 in place of the element data processing unit 22, and an image generation unit 116 in place of the image generation unit 24. Thus, the same components are assigned the same reference numerals and detailed descriptions thereof are omitted.

The ultrasonic diagnostic apparatus 110 includes the ultrasonic probe 12, the transmitting unit 14 and the receiving unit 16, which are connected to the ultrasonic probe 12, the A/D conversion unit 18, the element data storage unit 20, the setting information holding unit 21, the data processing unit 114, the setting changing unit 23, the image generation unit 116, the display control unit 26, the display unit 28, the control unit 30, the operation unit 32, and the storage unit 34.

In FIG. 12, the configuration of the data processing unit 114 is conceptually illustrated using a block diagram.

The data processing unit 114 includes a phasing addition unit 118, the delay time calculation unit 48, and a superimposition processing unit 120.

The phasing addition unit 118 performs phasing addition on element data read from the element data storage unit 20 to perform a receive-focusing process, and generates first reception data (unprocessed reception data).

Here, the phasing addition processing performed by the phasing addition unit 118 involves performing the receive-focusing process described above on a single piece of element data a plurality of times while changing a reference line to generate two or more pieces of unprocessed reception data for each piece of element data.

The superimposition processing unit 120 acquires the unprocessed reception data generated by the phasing addition unit 118, on the basis of information related to data processing, such as the number of pieces of data to be superimposed and the superimposition processing method.

Further, the superimposition processing unit 120 superimposes two or more pieces of unprocessed reception data in terms of reception time, that is, in such a manner that their times are aligned, on the basis of the delay times corresponding to the respective pieces of unprocessed reception data, which are calculated by the delay time calculation unit 48, to generate processed (second) reception data.

Specifically, the superimposition processing unit 120 superimposes, among the pieces of unprocessed reception data supplied from the phasing addition unit 118, pieces of unprocessed reception data subjected to phasing addition processing on the same line in accordance with the times at which the respective ultrasonic transducers receive the ultrasonic echoes, and generates processed reception data corresponding to a piece of unprocessed reception data.

Note that this processed reception data is a piece of processed data in the present invention.

The phasing addition unit 118 and the superimposition processing unit 120 will be described in more detail using parts (a) to (i) of FIG. 13 and parts (a) to (h) of FIG. 14.

First, the phasing addition processing performed in the phasing addition unit 118 will be described in detail using parts (a) to (i) of FIG. 13.

Parts (a), (d), and (g) of FIG. 13 are conceptual diagrams for describing individual receive elements, parts (b), (e), and (h) of FIG. 13 are conceptual diagrams illustrating element data obtained by each transmission and reception of ultrasonic waves, and parts (c), (f), and (i) of FIG. 13 are conceptual diagrams illustrating unprocessed reception data obtained by subjecting individual pieces of element data to phasing addition processing.

Note that parts (a) to (i) of FIG. 13 illustrate a state in which a reflection point is located on a line corresponding to the n-th element.

First, an example of the generation of two or more pieces of unprocessed reception data from a single piece of element data will be described using parts (a) to (c) of FIG. 13.

Part (a) of FIG. 13 is a diagram conceptually illustrating the vibrator array 36 in which a plurality of elements are arranged. In part (a) of FIG. 13, the positions of the elements are represented with the letter "n" and receive elements are represented with hatching. That is, part (a) of FIG. 13 illustrates that the (n−4)-th to (n+4)-th elements are receive elements, with the n-th element being the central element.

Part (b) of FIG. 13 is a diagram conceptually illustrating element data acquired by the receive elements illustrated in part (a) of FIG. 13. In addition, the positions in part (b) of FIG. 13 are displayed so as to correspond to the positions of the receive elements illustrated in part (a) of FIG. 13.

Note that, in the following description, element data obtained by using the n-th element as the central element is referred to as the n-th element data.

The phasing addition unit 118 reads the n-th element data from the element data storage unit 20, and performs phasing addition processing by using the line corresponding to the n-th element (hereinafter also referred to as the n-th line) as a reference line to generate the n(n)-th unprocessed reception data depicted in the center in part (c) of FIG. 13. The phasing addition unit 118 further performs phasing addition processing on the n-th element data by using the (n−2)-th line as a reference line to generate the n(n−2)-th unprocessed reception data depicted to the left in part (c) of FIG. 13. Likewise, the phasing addition unit 118 performs phasing addition processing on the n-th element data by respectively using the (n−1)-th, (n+1)-th, and (n+2)-th lines as reference lines to generate the n(n−1)-th unprocessed reception data, the n(n+1)-th unprocessed reception data, and the n(n+2)-th unprocessed reception data.

Here, reception data generated by subjecting, for example, the x-th element data to phasing addition by using the y-th line as a reference is expressed herein as the x(y)-th reception data.

Specifically, the phasing addition unit 118 of this embodiment performs, for a single piece of element data, phasing addition processing on each of five lines in total, including the lines corresponding to two elements located to the left and right of the central element and the line corresponding to the central element of the receive elements corresponding to the element data, to generate five pieces of unprocessed reception data, as illustrated in part (c) of FIG. 13.

Accordingly, as illustrated in parts (d) to (f) of FIG. 13, for the (n−1)-th element data, phasing addition processing is performed on each of the (n−3)-th to (n+1)-th lines centered on the (n−1)-th line to generate five pieces of unprocessed reception data illustrated in part (f) of FIG. 13. In addition, as illustrated in parts (g) to (i) of FIG. 13, for the (n+1)-th element data, phasing addition processing is performed on each of the (n−1)-th to (n+3)-th lines centered on the (n+1)-th line to generate five pieces of unprocessed reception data illustrated in part (i) of FIG. 13.

In this way, the phasing addition unit 118 performs phasing addition processing on necessary element data a plurality of times to generate a plurality of pieces of unprocessed reception data.

The phasing addition unit 118 supplies the pieces of unprocessed reception data to the superimposition processing unit 120.

Note that the number of pieces of unprocessed reception data generated from a single piece of element data in the phasing addition unit 118 is not particularly limited and may be determined, as appropriate, in accordance with the performance of the apparatus, the required processing speed (such as the frame rate), the image quality, and so on.

In addition, it is also preferable that the phasing addition unit 118 generate, in accordance with the width of the ultrasonic beam, a number of pieces of unprocessed reception data corresponding to the number of lines corresponding to the width.

Specifically, it is preferable that, when the number of superimpositions in the superimposition processing performed in the superimposition processing unit 120, described below, is to be caused to vary in accordance with the width of the ultrasonic transmit beam, phasing addition be performed, for each piece of element data, by using, as a reference, the central element of the receive elements corresponding to the piece of element data in accordance with the number of superimpositions and, in addition, phasing addition processing be performed a number of times corresponding to the number of superimpositions with an element used as a reference of the phasing addition being shifted.

For example, when the number of superimpositions is 11, phasing addition processing is performed by using as references the central element of the receive elements corresponding to the element data to be processed and five elements located to the left and right of the central element.

This enables the effect of superimposition to be sufficiently exerted and can reduce the amount of data to be stored.

Note that, when the number of superimpositions in the data processing unit 114 varies depending on the depth, the phasing addition unit 118 may generate a plurality of pieces of unprocessed reception data by changing the number of times phasing addition processing is performed on a single piece of element data depending on the depth or may generate a number of pieces of unprocessed reception data corresponding to the maximum width of the ultrasonic beam regardless of the depth.

Specifically, it is preferable that the phasing addition unit 118 generate a number of pieces of unprocessed reception data corresponding to three to ten lines for a single piece of element data.

In addition, while there is also no particular limitation on the lines to be subjected to phasing addition processing, it is preferable that phasing addition processing be performed, for each piece of element data, by using, as references, the line of the central element of the receive elements corresponding to the element data and the lines of two or more elements horizontally adjacent to the central element.

Next, the superimposition processing performed in the superimposition processing unit 120 will be described in detail using parts (a) to (h) of FIG. 14.

Parts (a) and (e) of FIG. 14 are each a conceptual diagram illustrating unprocessed reception data to be subjected to superimposition, parts (b) and (f) of FIG. 14 are conceptual diagrams for describing their delay times, parts (c) and (g) of FIG. 14 are conceptual diagrams for describing the state of superimposed unprocessed reception data, and parts (d) and (h) of FIG. 14 are conceptual diagrams for describing the result of superimposition of the unprocessed reception data.

Note that the example illustrated in parts (a) to (h) of FIG. 14 is an example in which the number of superimpositions in the superimposition processing unit 120 is five.

In addition, the unprocessed reception data illustrated in parts (a) and (e) of FIG. 14 is a conceptual representation of unprocessed reception data for which the reflection point is located on the n-th line.

As illustrated in part (a) of FIG. 14, in order to generate processed reception data corresponding to the n(n)-th unprocessed reception data, the superimposition processing unit 120 acquires five pieces of unprocessed reception data (the n−2(n)-th unprocessed reception data, the n−1(n)-th unprocessed reception data, the n(n)-th unprocessed reception data, the n+1(n)-th unprocessed reception data, and the n+2(n)-th unprocessed reception data), which are pieces of unprocessed reception data generated as a result of subjecting different pieces of element data to phasing addition processing by using the n-th line as a reference.

The superimposition processing unit 120 performs delay-time correction on each of the five pieces of unprocessed reception data on the basis of the delay time calculated by the delay time calculation unit 48 (part (b) of FIG. 14), superimposes the resulting pieces of unprocessed reception data (part (c) of FIG. 14), and sums or averages the resulting pieces of unprocessed reception data to generate processed reception data corresponding to the n(n)-th unprocessed reception data (part (d) of FIG. 14). The resulting processed reception data is processed reception data corresponding to the n-th element (line).

Here, the superimposition processing unit 120 supplies setting information such as the number of superimpositions of processed reception data to the setting information holding unit 21.

In addition, if a measurement condition is changed, the superimposition processing unit 120 performs superimposition processing on the basis of the setting changed by the setting changing unit 23 to generate processed reception data.

This can prevent a large change in image lightness or frame rate before and after the change of the measurement condition.

Similarly, in order to generate processed reception data corresponding to the (n−1)-th line, the superimposition processing unit 120 acquires five pieces of unprocessed reception data (part (e) of FIG. 14), which are generated as a result of performing phasing addition processing by using the (n−1)-th line as a reference.

The superimposition processing unit 120 performs delay-time correction on each of the five pieces of unprocessed reception data on the basis of the delay time (part (f) of FIG. 14), superimposes the resulting pieces of unprocessed reception data (part (g) of FIG. 14), and sums or averages the resulting pieces of unprocessed reception data to generate the (n−1)-th processed reception data (part (h) of FIG. 14).

Here, as in parts (a) to (d) of FIG. 14, if pieces of unprocessed element data on which phasing addition processing has been performed by using as a reference a line (the n-th line) on which the reflection point is located are subjected to delay-time correction and are then superimposed, the phases of the signals from the reflection point are matched. Thus, as a result of the superimposition processing, a value (high-brightness value) with a signal (true signal) from the reflection point being enhanced is exhibited. (Part (d) of FIG. 14).

In contrast, as in parts (e) to (h) of FIG. 14, if pieces of unprocessed element data on which phasing addition processing has been performed by using as a reference a line (the (n−1)-th line) on which the reflection point is not located are subjected to delay-time correction, the phases of signals (ghost signals) from the reflection point are not matched. Thus, as a result of superimposition, the signals cancel each other out, resulting in a signal having a small value (part (h) of FIG. 14).

Also for the other elements (lines), two or more pieces of unprocessed reception data on which phasing addition processing has been performed by using as a reference a line corresponding to an element of interest, where the element of interest is each of these elements, are read and are subjected to superimposition processing based on the delay times to enhance true signals whilst allowing ghost signals to cancel out, thereby enabling a reduction in the effect of the ghost signals.

Accordingly, processed reception data is subjected to detection processing and the like to generate an ultrasound image. This enables an ultrasound image to be generated from reception data that is free of influence of ghosting and for which it is equivalent to saying that every point on a sound ray is brought into focus. Thus, a high-brightness, high-quality ultrasound image with good sharpness can be generated.

In this manner, it is also possible to perform superimposition processing (multi-line processing) by using unprocessed reception data obtained as a result of subjecting element data to phasing addition processing. Note that the configuration in which phasing addition processing is followed by superimposition processing is preferable because the amount of data to be held (stored) can be reduced.

The data processing unit 114 supplies the generated processed reception data to the image generation unit 116.

The image generation unit 116 includes the detection processing unit 40, the DSC 42, the image processing unit 44, and the image memory 46.

In the image generation unit 116, the detection processing unit 40 performs attenuation correction and envelope detection processing on the reception data to generate B-mode image data. In addition, the DSC 42 raster-converts the B-mode image data into image data that supports a normal television signal scanning system, and the image processing unit 44 performs predetermined processing such as gradation processing.

The image processing unit 44 stores the generated B-mode image data in the image memory 46, and/or delivers it to the display control unit 26 to display a B-mode image of the subject on the display unit 28.

While an acoustic wave processing apparatus, a signal processing method, and a non-transitory computer readable recording medium storing a program of the present invention have been described in detail, it is needless to say that the present invention is not limited to the examples described above and various improvements or modifications may be made within the scope not departing from the gist of the present invention.

For example, the element data storage unit 20, which stores element data for one image, may not be included and transmission and reception of ultrasonic waves may be performed, for a single element of interest, a required number of times every time multi-line processing is performed.

REFERENCE SIGNS LIST

10, 110 ultrasonic diagnostic apparatus
12 (ultrasonic wave) probe
14 transmitting unit
16 receiving unit
18 A/D conversion unit
20 element data storage unit
21 setting information holding unit
22 element data processing unit
23 setting changing unit
24, 116 image generation unit
26 display control unit
28 display unit
30 control unit
32 operation unit
34 storage unit
36 vibrator array
38, 118 phasing addition unit
40 detection processing unit
42 DSC
44 image processing unit
46 image memory
48 delay time calculation unit
49, 120 superimposition processing unit
52 element
54 reflection point
56, 64 ultrasonic beam
58 focal point
60 receive path
61 transmit path
62 element data
66 true element data
68 ghost element data
114 data processing unit

What is claimed is:

1. An acoustic wave processing apparatus comprising:
a probe unit having a plurality of elements arranged therein, the probe unit being configured to transmit an acoustic wave beam, receive an acoustic wave echo reflected by an inspection object, and output an analog element signal corresponding to the received acoustic wave echo; and
a processor configured to:
cause the probe unit to perform a plurality of times an operation of transmitting the acoustic wave beam by using two or more elements among the plurality of elements as transmit elements to form a predetermined transmit focal point,
receive an acoustic echo corresponding to each transmission of the acoustic beam with two or more elements among the plurality of elements as reception elements, receive analog element signals output from the reception elements, and perform predetermined processing on the analog element signals,
perform A/D conversion on the analog element signals which are processed to convert the analog element signals to first element data as a digital element signal,
select two or more pieces of data from among a plurality of pieces of the first element data which is output or from among a plurality of pieces of first reception data generated by performing phasing addition processing on the first element data and perform superimposition processing on the selected two or more pieces of data to generate processed data,
generate an acoustic wave image on the basis of the processed data which is generated,
cause a display unit to display the generated acoustic wave image,
hold a setting information on at least one of a transmit condition of the acoustic wave beam, a receiving condition of the acoustic echo, setting information with which the processed data is generated, setting information with which the acoustic wave image is generated, and setting information with which the acoustic wave image is displayed, and when a measurement condition is changed, change setting of at least one of the transmit condition of the acoustic wave beam, the receiving condition of the acoustic echo, the setting information with which the processed data is generated, the setting information with which the acoustic wave image is generated, and the setting information with which the acoustic wave image is displayed on the basis of the setting information which is held, the setting being related to the acoustic wave image generated on the basis of the processed data, wherein the processor is further configured to:

perform phasing addition on each of the pieces of first element data by using at least two elements as references to generate at least two pieces of first reception data for each of the pieces of first element data, select two or more pieces of first reception data from among the plurality of pieces of first reception data, and superimpose the selected two or more pieces of first reception data in accordance with reception times at which the elements receive the acoustic wave echo to generate second reception data, and superimpose the two or more pieces of first reception data, the two or more pieces of first reception data being generated from the pieces of first element data, which are different from each other, and being generated by subjecting the different pieces of first element data to phasing addition processing by using the same element as a reference for each different piece of first element data subjected to phasing addition.

2. The acoustic wave processing apparatus according to claim 1, wherein the processor is further configured to change the setting of at least one of the transmit condition of the acoustic wave beam, the receiving condition of the acoustic echo, the setting information with which the processed data is generated, the setting information with which the acoustic wave image is generated, and the setting information with which the acoustic wave image is displayed on the basis of setting information on the setting information with which the processed data is generated which is held.

3. The acoustic wave processing apparatus according to claim 1, wherein the processor is further configured to change the setting information with which the processed data is generated on the basis of the setting information held.

4. The acoustic wave processing apparatus according to claim 2, wherein the processor is further configured to change the setting information with which the processed data is generated on the basis of the setting information held.

5. The acoustic wave processing apparatus according to claim 1, wherein the processor is further configured to select two or more pieces of first element data from among the plurality of pieces of first element data, and superimpose the selected two or more pieces of first element data in accordance with reception times at which the elements receive the acoustic wave echo and positions of the elements to generate second element data.

6. The acoustic wave processing apparatus according to claim 2, wherein the processor is further configured to select two or more pieces of first element data from among the plurality of pieces of first element data, and superimpose the selected two or more pieces of first element data in accordance with reception times at which the elements receive the acoustic wave echo and positions of the elements to generate second element data.

7. The acoustic wave processing apparatus according to claim 3, wherein the processor is further configured to select two or more pieces of first element data from among the plurality of pieces of first element data, and superimpose the selected two or more pieces of first element data in accordance with reception times at which the elements receive the acoustic wave echo and positions of the elements to generate second element data.

8. The acoustic wave processing apparatus according to claim 4, wherein the processor is further configured to select two or more pieces of first element data from among the plurality of pieces of first element data, and superimpose the selected two or more pieces of first element data in accordance with reception times at which the elements receive the acoustic wave echo and positions of the elements to generate second element data.

9. The acoustic wave processing apparatus according to claim 2, wherein the processor is further configured to perform phasing addition on each of the pieces of first element data by using at least two elements as references to generate at least two pieces of first reception data for each of the pieces of first element data, and select two or more pieces of first reception data from among the plurality of pieces of first reception data, and superimpose the selected two or more pieces of first reception data in accordance with reception times at which the elements receive the acoustic wave echo to generate second reception data.

10. The acoustic wave processing apparatus according to claim 3, wherein the processor is further configured to perform phasing addition on each of the pieces of first element data by using at least two elements as references to generate at least two pieces of first reception data for each of the pieces of first element data, and select two or more pieces of first reception data from among the plurality of pieces of first reception data, and superimpose the selected two or more pieces of first reception data in accordance with reception times at which the elements receive the acoustic wave echo to generate second reception data.

11. The acoustic wave processing apparatus according to claim 4, wherein the processor is further configured to perform phasing addition on each of the pieces of first element data by using at least two elements as references to generate at least two pieces of first reception data for each of the pieces of first element data, and select two or more pieces of first reception data from among the plurality of pieces of first reception data, and superimpose the selected two or more pieces of first reception data in accordance with reception times at which the elements receive the acoustic wave echo to generate second reception data.

12. The acoustic wave processing apparatus according to claim 1, wherein the setting information with which the processed data is generated comprises information on at least one of the number of pieces of data to be superimposed, apodization, sound velocity, and delay time.

13. The acoustic wave processing apparatus according to claim 1, wherein the change of the measurement condition comprises changing a type of a probe including the probe unit.

14. The acoustic wave processing apparatus according to claim 1, wherein the change of the measurement condition comprises changing the predetermined transmit focal point of the acoustic wave beam which is transmitted.

15. The acoustic wave processing apparatus according to claim 1, wherein the setting information with which the acoustic wave image is generated comprises a gain value for amplifying the processed data, and
wherein the processor is further configured to change a setting of the gain value on the basis of information on the number of pieces of data to be superimposed in the superimposition processing.

16. The acoustic wave processing apparatus according to claim 1, wherein the processor is further configured to cause the probe unit to transmit the acoustic wave beam the plurality of times by at least either changing an element serving as a center or changing a transmit direction of the acoustic wave beam.

17. A signal processing method for the examining an inspection object by using a probe unit having a plurality of elements arranged therein, the probe unit being configured to transmit an acoustic wave beam, receive an acoustic wave echo reflected by the inspection object, and output an analog element signal corresponding to the received acoustic wave echo, the signal processing method comprising:
a transmitting step of performing the plurality of times the operation of transmitting the acoustic wave beam by using two or more elements among the plurality of elements of the probe unit as transmit elements to form the predetermined transmit focal point;
a receiving step of receiving the acoustic echo corresponding to each transmission of the acoustic beam with two or more elements among the plurality of elements as reception elements, receiving analog element signals output from the reception elements, and performing predetermined processing on the analog element signals;
an A/D conversion step of performing A/D conversion on the analog element signals which are processed to convert the analog element signals to first element data as the digital element signal;
a data processing step of selecting two or more pieces of data from among the plurality of pieces of the first element data which is output in the ND or from among the plurality of pieces of first reception data generated by performing phasing addition processing on the first element data, and performing superimposition processing to generate processed data;
an image generating step of generating the acoustic wave image on the basis of the processed data which is generated;
a display control step of causing the display unit to display the generated acoustic wave image;
a setting information holding step of holding a setting information on at least one of a transmit condition of the acoustic wave beam, a receiving condition of the acoustic echo, setting information with which the processed data is generated, setting information with which the acoustic wave image is generated, and setting information with which the acoustic wave image is displayed; and
a setting information changing step of, when the measurement condition is changed, changing the setting of at least one of the transmit condition of the acoustic wave beam, the receiving condition of the acoustic echo, the setting information with which the processed data is generated, the setting information with which the acoustic wave image is generated, and the setting information with which the acoustic wave image is displayed on the basis of the setting information which is held, the setting being related to the acoustic wave image generated on the basis of the processed data,
wherein the method further comprises:
performing phasing addition on each of the pieces of first element data by using at least two elements as references to generate at least two pieces of first reception data for each of the pieces of first element data,
selecting two or more pieces of first reception data from among the plurality of pieces of first reception data, and superimpose the selected two or more pieces of first reception data in accordance with reception times at which the elements receive the acoustic wave echo to generate second reception data, and
superimposing the two or more pieces of first reception data, the two or more pieces of first reception data being generated from the pieces of first element data, which are different from each other, and being generated by subjecting the different pieces of first element data to phasing addition processing by using the same element as a reference for each different piece of first element data subjected to phasing addition.

18. A non-transitory computer readable recording medium configured to store a signal processing program, the signal processing program being a program for causing a computer to execute a signal processing method for an acoustic wave processing apparatus for examining an inspection object by using a probe unit having a plurality of elements arranged therein, the probe unit being configured to transmit an acoustic wave beam, receive an acoustic wave echo reflected by the inspection object, and output the analog element signal corresponding to the received acoustic wave echo, the signal processing program causing the computer to execute:
a transmitting step of performing the plurality of times the operation of transmitting the acoustic wave beam by using two or more elements among the plurality of elements of the probe unit as transmit elements to form the predetermined transmit focal point;
a receiving step of receiving the acoustic echo corresponding to each transmission of the acoustic beam with two or more elements among the plurality of elements as reception elements, receiving analog element signals output from the reception elements, and performing predetermined processing on the analog element signals;
an A/D conversion step of performing A/D conversion on the analog element signals which are processed to convert the analog element signals to first element data as the digital element signal;
a data processing step of selecting two or more pieces of data from among the plurality of pieces of the first element data which is output or from among the plurality of pieces of first reception data generated by performing phasing addition processing on the first element data, and performing superimposition processing to generate processed data;
an image generating step of generating the acoustic wave image on the basis of the processed data which is generated;
a display control step of causing the display unit to display the generated acoustic wave image;
a setting information holding step of holding a setting information on at least one of a transmit condition of the acoustic wave beam, a receiving condition of the acoustic echo, setting information with which the processed data is generated, setting information with which the acoustic wave image is generated, and setting information with which the acoustic wave image is displayed; and a setting information changing step of, when the measurement condition is changed, changing the setting of at least one of the transmit condition of the acoustic wave beam, the receiving condition of the acoustic echo, the setting information with which the processed data is generated, the setting information with which the acoustic wave image is generated, and the setting information with which the acoustic wave image is displayed on the basis of the setting information which is held, the setting being related to the acoustic wave image generated on the basis of the processed data, wherein the signal processing program further causing the computer to execute:

perform phasing addition on each of the pieces of first element data by using at least two elements as references to generate at least two pieces of first reception data for each of the pieces of first element data, select two or more pieces of first reception data from among the plurality of pieces of first reception data, and superimpose the selected two or more pieces of first reception data in accordance with reception times at which the elements receive the acoustic wave echo to generate second reception data, and superimpose the two or more pieces of first reception data, the two or more pieces of first reception data being generated from the pieces of first element data, which are different from each other, and being generated by subjecting the different pieces of first element data to phasing addition processing by using the same element as a reference for each different piece of first element data subjected to phasing addition.

* * * * *